United States Patent [19]
Mynott

[11] Patent Number: 5,928,640
[45] Date of Patent: Jul. 27, 1999

[54] USE OF ENZYMES, ESPECIALLY BROMELAIN, IN THE TREATMENT OF DIARRHOEA

[75] Inventor: Tracey Leahanne Mynott, Richmond, United Kingdom

[73] Assignee: Cortecs Limited, Isleworth, United Kingdom

[21] Appl. No.: 08/360,693

[22] PCT Filed: Jun. 30, 1993

[86] PCT No.: PCT/GB93/01374

§ 371 Date: Feb. 14, 1995

§ 102(e) Date: Feb. 14, 1995

[87] PCT Pub. No.: WO94/00147

PCT Pub. Date: Jan. 6, 1994

[30] Foreign Application Priority Data

Jun. 30, 1992 [GB] United Kingdom ............... 921386
Apr. 20, 1993 [GB] United Kingdom ............... 9308164
Jun. 25, 1993 [GB] United Kingdom ............... 9313189

[51] Int. Cl.$^6$ ................................... A61K 38/48
[52] U.S. Cl. .................... 424/94.63; 424/94.64; 424/94.65; 424/94.66; 424/94.67
[58] Field of Search ............... 424/94.63, 94.64, 424/94.65, 94.66, 94.67

[56] References Cited

U.S. PATENT DOCUMENTS

| | | | |
|---|---|---|---|
| 3,574,819 | 4/1971 | Gross et al. ................... | 424/94.65 |
| 5,260,074 | 11/1993 | Sipos ............................. | 424/94.2 |
| 5,302,400 | 4/1994 | Sipos ............................. | 424/94.21 |

FOREIGN PATENT DOCUMENTS

| | | |
|---|---|---|
| 2361116 | 10/1978 | France . |
| 2414554 | 10/1979 | France . |
| 1161439 | 8/1969 | United Kingdom . |
| 88/01506 | 3/1988 | WIPO . |
| 88/01512 | 3/1988 | WIPO . |
| 93/01800 | 2/1993 | WIPO . |

OTHER PUBLICATIONS

Bromelains, Enzymes Choleretics and Other Digestive Agents , p. 646.
Fasano et al., "Vibrio Cholerae Produces A Second Enterotoxin, Which Affects Intestinal Tight Junctions", *Proc. Natl. Acad. Sci. USA*, vol. 88:5242–5246, (1991).
Christiansen et al., "Microvillus Membrane Vesicles From Pig Small Intestine", *Biochimica et Biophysica Acta*, vol. 647:188–195, (1981).
Field et al., "Ion Transport In Rabbit Ileal Mucosa. I. Na and Cl Fluxes And Short–Circuit Current", *American Journal Of Physiology*, vol 220:1388–1396, (1971).
Schmitz et al., "Purification Of The Human Intestinal Brush Border Membrane", *Biochimica et Biophysica Acta*, vol. 323:98–112, (1973).
Rubino et al., "Intestinal Transport Of Amino Acid Residues Of Dipeptides", *The Journal Of Biological Chemistry*, vol. 246:3542–3548, (1971).
Ussing et al., "Active Transport Of Sodium As The Source Of Electric Current In The Short–Circuited Isolated Frog Skin", *Acta Phys. Scandinav.*, vol. 23:11–127, (1950).
Ritonja et al., "Stem Bromelain: Amino Acid Sequence And Implications For Weak Binding Of Cystatin", *Elsevier Science Publishers B.V*, vol. 247:419–424, (1989).
Taussig et al., "Bromelain, The Enzyme Complex Of Pineapple (*Ananas Comosus*) And Its Clinical Application, An Update", *Journal of Ethnopharmacology*, vol. 22:191–203, (1989).
Andree et al., "Pilus–Mediated Binding of Bovine Enterotoxigenic *Escherichia coli* To Calf Small Intestinal Mucins", *Infection And Immunity*, vol. 55:1216–1223, (1987).
Laux et al., "Identification And Characterization Of Mouse Small Intestine Mucosal Receptors For *Escherichia coli* K–12 (K88ab)", vol. 52:18–25, (1986).
J. Carlsen et al., "Purification of Microvillus Membrane Vesicles from Pig Small Intestine by Immunoadsorbent Chromatography", Biochimica et Biophysica Acta, 689:12–20 (1982).
M. Field, "Ion transport in rabbit ileal mucosa. II. Effects of cyclic 3', 5'–AMP", American Journal of Physiology, 221(4):992–997 (1971).
R. Gots et al., "Indomethacin Inhibition of *Salmonella typhimurium, Shigella flexneri*, and Cholera Mediated Rabbit Ileal Secretion", Jour. of Infectious Diseases, 130(3):280–284 (1974).
S. Taussig et al., "Bromelain, the enzyme complex of pineapple and its clinical application, an update", Joural of Ethnopharmacology, 22:191–203 (1988).
A. Finck et al., "Prevention of Cholera–induced Intestinal Secretion in the Cat by Aspirin", Nature, 238:273–274 (1972).
J. Peterson et al., "Inhibitory effect of ibuprofen on the cholera toxin–induced cyclic AMP response in Chinese hamster ovary cells", FEMS Microbiology Letters, 56:139–144 (1988).
M. Chandler et al., "An Investigation of the Use of Urease–Antibody Conjugates in Enzyme Immunoassays", Jour. of Immunological Methods, 53:187–194 (1982).
Martindale, Enzymes Choleretics and other Digestive Agents, 28th edition, p. 646.

*Primary Examiner*—Jean C. Witz
*Attorney, Agent, or Firm*—Foley & Lardner

[57] ABSTRACT

Enzymes, especially proteolytic enzymes such as bromelain, have been found to inhibit the action of heat-labile toxin (LT) of enterotoxigenic *Escherichia coli*. They are therefore useful in the prophylaxis, management and treatment of diarrhoea in humans.

8 Claims, 15 Drawing Sheets

USE OF ENZYMES, ESPECIALLY BROMELAIN, IN THE TREATMENT OF DIARRHOEA

This invention relates to the prophylaxis, management and treatment of diarrhoea.

Diarrhoea, particularly traveller's diarrhoea, can be caused by a change in the microorganisms of the gut. Enterotoxigenic *Escherichia coli* (ETEC) infections are common and, as many holiday makers and business travellers can testify, can leave the sufferer ambivalent about the virtue of leaving his native country. *E. coli* is not the only aetiological agent: more seriously, *Vibrio cholerea,* the causative agent of cholera, can cause diarrhoea as part of its sometimes fatal mode of action.

Enterotoxigenic strains of *E. coli* (ETEC) are characterised by their ability to produce a heat-labile toxin (LT) and/or heat-stable toxin (ST). Some ETEC strains also produce pilus adhesins called colonisation factor antigens. These adhesins promote attachment of ETEC strains to the small intestinal mucosa, thereby facilitating colonisation and delivery of enterotoxin. Diarrhoeal disease is ultimately dependent on production and efficient delivery of enterotoxin.

The enterotoxins stimulate secretion by cells by activation of signal pathways. Internal signals within cells are carried by "second messengers". At least three signal pathways are known to be important for secretion. One pathway employs the second messenger cyclic adenosine monophosphate (cyclic AMP). Another employs the second messenger cyclic guanosine monophosphate (cyclic GMP). These two messengers are referred to as cyclic nucleotides. The third signal pathway ($CA^{2+}$-dependent pathway) requires $Ca^{2+}$ as the second messenger.

The mode of action of LT is virtually identical to that of cholera toxin (CT), which has been well documented. Briefly, the B protomer binds to a ganglioside receptor GM1 [galactosyl-N-acetylgalactosaminyl-(N-acetyl-neuraminyl) galactosylglucosylceramide] located on the brush border membrane. Recent studies have shown that LT also binds to a structurally related glycoprotein to which CT does not bind. Binding is followed by translocation of the A subunit through the membrane and release of the A1 fragment into the cytosol after proteolytic activation. Adenylate cyclase activity is stimulated following catalysing the NAD-dependent cyclase complex. As a result, adenylate cyclase is locked into an active form through inhibition of an inherent feed-back regulatory mechanism which normally involves the hydrolysis of GTP to GDP and Pi. Inactivation of the regulatory subunit leads to increased levels of the second messenger, cyclic AMP. cAMP activates an enzyme called protein kinase A which, in turn, phosphorylates proteins. The phosphorylation of proteins (that is, the addition of a phosphate group) results in the opening of chloride channels and therefore secretion. Increased levels of cAMP is also known to inhibit the absorption of NaCl.

The mode of action of ST is less well understood than that of LT. STs produced by ETEC are a heterogeneous group of molecules having a molecular weight of from about 2000 to 5000 Da and which are non-antigenic in their native state. An example of a common ST is ST I which can be either an 18 or a 19 amino acid peptide. In contrast to LT, which activates adenylate cyclase of intestinal cells, ST I stimulates only the particulate form of intestinal guanylate cyclase. The action of ST I is almost instantaneous. The initial step in the biological action of ST is its interaction with membrane-bound guanylate cyclase in the cells, leading to an increase in the intracellular concentration of cyclic GMP followed by activation of cyclic GMP-dependent protein kinase (protein kinase G). This culminates in the inhibition of $Na^+$ absorption and opening of chloride channels and, hence, stimulation of $Cl^-$ secretion. ST-induced fluid secretion is relatively short-lived and is readily reversed, in contrast to the delayed but sustained and irreversible effects of LT on adenylate cyclase and fluid secretion. The intestinal ST I receptor has been shown to be a guanyl cyclase although other proteins or glycoproteins may also have a role.

Intestinal transcellular absorption and secretion of electrolytes is driven by the $Na^+/K^+$ ATPase pump, located in the enterocyte basolateral membrane. Water flows passively with electrolytes in response to osmotic gradients, and $Na^+$ and $Cl^-$ are the predominant ions involved in the absorption and secretion of water. The absorptive and secretory processes in the small intestine are separated. In general, electrolytes and water are secreted from crypt enterocytes, and reabsorption takes place through villus enterocytes. Normally, secretion and absorption are balanced to prevent dehydration. The diarrhoeal response caused by LT and CT results from stimulation of a cAMP-mediated active secretory mechanism (i.e. the cAMP pathway). The diarrhoeal response caused by ST is from stimulation of the cGMP pathway. cAMP and cGMP exert an anti-absorptive effect on villus cells by inhibiting uptake of NaCl, and in addition stimulates active chloride secretion by crypt cells (by opening of the chloride channels). When the level of secretion increases beyond the ability of the colon to reabsorb water and electrolytes lost from the small intestine, diarrhoea results that can lead to severe dehydration and, eventually in extreme cases, death.

If subjects are adequately rehydrated after infection by CT, LT or ST, examination of the intestinal mucosa shows no bacterial invasion, no infiltration of leukocytes, and no capillary damage, even at the ultrastructural level. Consistent with the normal morphology, absorptive processes for nutrients do not seem to be impaired.

A vast accumulation of knowledge has been attained on the mechanisms of attachment and role of enterotoxins in pathogenesis of enterotoxigenic *Escherichia coli* (ETEC) infections. Despite this knowledge, safe and effective prophylaxis against ETEC diarrhoea or treatment that can counteract the large fluid losses sometimes observed, are unavailable. Several studies have shown the efficacy of antimicrobial drugs such as doxycycline and trimethoprim/sulfamethoxazole in prophylaxis of traveller's diarrhoea. However, use of these agents has not been encouraged because of the risks of side effects, including hypersensitivity reactions, and because of the rapid emergence of drug resistant flora in the stools of these patients. Subsalicylate bismuth is partially effective prophylaxis against traveller's diarrhoea. However, objectionable taste, constipation, and nausea were observed in patients taking the liquid formulation. In addition, many travellers find carrying large amounts of liquid medication inconvenient. Current means of treating diarrhoeal disease centre around the use of synthetic opiates such as loperamide, alkaloids, for example berberine sulphate, adsorbents and oral rehydration therapy.

A considerable amount of attention in recent years has been directed towards immunoprophylaxis. Significant protection against diarrhoea caused by ETEC following vaccination with a combination of formalin and heat-inactivated whole *Vibrio cholerae* cells and the purified B subunit of cholera toxin has been reported. Other efforts to develop vaccines against ETEC infection centre around the use of colonisation factor antigens (CFAS) as vaccine candidates. As colonisation factors are is antigenically distinct, potential vaccines, must be multivalent. A prototype ETEC vaccine that contains known CFAs and outer membrane antigens associated with ETEC is being developed. To be completely effective, though, a vaccine would have to deal with all the adhesive factors synthesised by ETEC strains in the developing areas.

While the prospect of effective immunisation against diarrhoeal diseases of humans is appealing, effective vaccines are not expected to he available in the near future.

A further problem is that diarrhoea is not necessarily caused by microorganisms but may also be induced by other secretagogues. Other secretagogues include hormones, neurotransmitters, bile salts, fatty acids and nutrients. Examples of diarrhoea include osmotically induced diarrhoea which is caused by lactose intolerance, malabsorption and diarrhoea caused by congential disorders. Of course, the antimicrobial drugs which are so often used in the treatment of infectious diarrhoea are completely ineffective in the treatment of non-infectious diarrhoea and the idea of immunisation is also inapplicable. Alternative approaches to the treatment and prevention of ETEC and non-infectious diarrhoea are therefore being pursued.

The present invention relates to such an alternative approach, and is based on the remarkable discovery that such enzymes as lytic enzymes, especially proteolytic enzymes and mixtures of enzymes such as bromelain and, in particular, stem bromelain protease which is a component of bromelain can reduce toxin binding activity and can inhibit the secretory effect of toxins such as LT and CT and also toxins such as ST. This is in spite of the fact that, as discussed above, ST has a very different mode of action from LT and CT. As an added benefit, it appears that such enzymes can prevent attachment of enterotoxigenic bacteria to the human intestinal lining. Even more surprisingly, such enzymes also seem to inhibit secretion induced by other secretagogues and, thus, may also be effective in the treatment of other, non-infectious, types of diarrhoea.

According to a first aspect of the present invention, there is provided the use of a lytic or other enzyme in the manufacture of a medicament for the prevention, management or treatment of diarrhoea in humans.

WO-A-8801512 teaches that bromelain or other enzymes could be used in the treatment of scour in piglets, but no disclosure was made either of the treatment of diarrhoea in humans or of the way in which the enzyme interferes with the diarrhoeal response to the toxin or other secretagogue. In fact, Martindale (28th Edition, page 646) states that bromelain may actually cause diarrhoea in humans and so provides a powerful disincentive to investigating the use of bromelain or other proteolytic enzymes in the treatment of that condition.

Experiments which led to the making of this invention have shown, by the use of an ex vivo rabbit intestinal tissue model in Ussing chambers, that bromelain and similarly acting enzymes significantly inhibited the secretory effect of LT, CT and also ST; more specifically, bromelain and other proteases completely inhibited the net anion flux of $Cl^-$, and hence the secretagogue effect of toxins such as LT and CT and also ST and other secretagogues unrelated to microorganisms. The proposed mechanism of action of the enzymes is that they prevent attachment of toxin by modification of the toxin receptors located on the brush border membrane. It is also hypothesised that these enzymes have an additional mechanism for inhibiting fluid secretion since they appear to inhibit secretion induced by prostaglandin $E_2$ and by other secretagogues that do not interact with cellular receptors, namely theophylline, 8-Br-cGMP, 8-Br-cAMP and Ca-ionophore.

There is now evidence that proteolytic enzymes such as bromelain and stem bromelain protease, which is a component of bromelain, have an effect on cyclic nucleotide pathways and this is explained more fully in the examples below. However, data indicate that the enzymes can also inhibit secretion by factors which do not require cyclic nucleotides. For example, it seems possible that they may also inhibit secretion by operating on the calcium dependent pathways. It is therefore possible that the enzymes may act, not on the different cyclic nucleotide pathways themselves but at the final step of the pathways which may be at the cell surface.

One theory which may explain the anti-secretory activity of these enzymes is that, in fact, bromelain or, specifically, the stem bromelain protease component of bromelain may have some effect on the chloride or other channels either to prevent the channels from opening or to block them. Either of these actions would account for the anti-secretory action of the enzymes but it should be stressed that the efficacy of enzymes such as bromelain and stem bromelain protease in the treatment of diarrhoea is not dependent on the accuracy of this proposal.

However, the significant point about these observations is that enzymes such as bromelain and stem bromelain protease will inhibit secretion caused by toxins and other secretagogues which cause diarrhoea by different mechanisms.

The enhancement of sodium absorption by glucose did not appear to be substantially affected by pre-treatment of tissue with bromelain in the same experimental model, this implies that protease does not result in extensive physiological damage to the mucosa. Histopathological and electron microscopic examination of tissue revealed no morphological abnormalities, thereby further confirming safety of the treatment.

Furthermore, there is also some evidence that proteolytic enzymes, particularly bromelain may also enhance absorption of secreted fluid and nutrients as well as inhibiting secretion.

In another experimental model, the effect of bromelain treatment on other physiologically important receptors was tested. The influx of the amino acids, glutamic acid, lysine and leucine and of the dipeptide, glycine-phenylalanine was investigated.

Results from the influx studies revealed that there was no interference with glucose, amino acid and dipeptide influx, supporting that bromelain has no adverse effect on receptors important for nutrient uptake. In fact, bromelain appeared to increase the absorption of these nutrients. This demonstrates that bromelain has an additional benefit other than just inhibiting secretion and that is that bromelain will also increase absorption. This remarkable discovery indicates that bromelain would be effective in aiding recovery from diarrhoea by increasing fluid and nutrient absorption.

The physiological principle of the World Health Organisation Oral Rehydration Solution (ORS) is to replace the loss of fluid, salts and nutrients lost due to diarrhoea. Death from diarrhoea is caused by dehydration because of fluid and nutrient loss. The active transport of nutrients across the brush border of the small intestine results in passive absorption of water and electrolytes. Bromelain in combination with nutrients, for example, those nutrients recommended by the World Health Organisation, would successfully assist in replacing the deficit of salts and water in diarrhoea and also actively induce reabsorption of intestinal secretions and thus reduce the volume and duration of diarrhoea.

A different experimental model, involving brush border vesicles, was used to investigate the use of protease in preventing attachment of colonisation factor antigen-positive bacteria (CFA-positive bacteria) using enzyme immunoassay procedures.

Enzymes useful in the invention include lytic enzymes. Glycolytic enzymes such as those with sialidase, glycosidase, amylase and cellulase activity may be preferred, as may lipolytic enzymes. Proteolytic enzymes may be particularly useful in the invention. Although bromelain is the preferred proteolytic enzyme, others may be useful. Cysteine proteases form a subclass of proteolytic enzymes which includes bromelain and papain. However, there is some evidence that papain may be inhibited by cystatins, whereas bromelain is not. Bromelain is therefore preferred. Other enzymes, such as trypsin, may be useful.

Bromelain is the collective name for the proteolytic enzymes found in the tissues of the plant Bromeliaceae. Bromelain is a mixture of various moieties derived from the stem of the pineapple (*Ananas comosus*). It contains at least two proteolytic enzymes but also non-proteolytic enzymes, including an acid phosphatase and a peroxidase; it may also contain amylase and cellulase activity. In addition, various other components are present, in particular, organically bound calcium. The known proteolytic enzymes of bromelain and papain share a high degree of amino acid sequence homology around the active centre, and evidence suggests that bromelain and papain use the same catalytic mechanism. Bromelain differs from papain, however, in having a different specificity of cleavage. In addition, the known proteolytic enzymes of bromelain are glycoproteins, whereas papain is a simple protein. Bromelain is reviewed by Taussig and Batkin (*J. Ethnopharmacol.* 22 191–203 (1988)).

As early as the fifteenth century, bromelain has been used as a digestive aid, as a cleansing agent to improve the texture of skin, and to treat wounds to promote healing. Recently, a vast accumulation of knowledge on its pharmacological and biological effects have resulted in bromelain being available for clinical use in man. In particular, bromelain is used as an adjunct in the treatment of soft tissue inflammation and oedema associated with trauma and surgery. Bromelain is available in various countries under the trademarks ANANASE FORTE, ANANASE, EXTRANASE, PROTEOLIS, RESOLVIT, ROGORIN, BROMASE and TRAUMANASE. In clinical use over a period of more than 30 years, there have been few reports of significant undesirable effects.

In the past, bromelain has been used as the crude mixture of enzymes and other components without attempts being made to ascribe its activity to any particular component of the mixture. However, the present inventors have now found that one particular component known as stem bromelain protease appears to be responsible for the anti-diarrhoea activity of bromelain.

Stem bromelain protease has been described by Ritonja et al (*Febs Letters,* 247, 419–424 (1989)) and has the amino acid sequence set out below (SEQ ID NO 1):

```
Ala Val Pro Gln Ser Ile Asp Trp Arg Asp Tyr Gly
1               5                   10
Ala Val Thr Ser Val Lys Asn Gln Asn Pro Cys Gly
            15                  20
Ala Cys Trp Ala Phe Ala Ala Ile Ala Thr Val Glu
```

-continued
```
        25              30              35
Ser Ile Tyr Lys Ile Lys Lys Gly Ile Leu Glu Pro
            40                      45
Leu Ser Glu Gln Gln Val Leu Asp Cys Ala Lys Gly
        50              55                  60
Tyr Gly Cys Lys Gly Gly Trp Glu Phe Arg Ala Phe
                65                  70
Glu Phe Ile Ile Ser Asn Lys Gly Val Ala Ser Gly
            75                  80
Ala Ile Tyr Pro Tyr Lys Ala Ala Lys Gly Thr Cys
85                  90                      95
Lys Thr Asp Gly Val Pro Asn Ser Ala Tyr Ile Thr
            100                 105
Gly Tyr Ala Arg Val Pro Arg Asn Asn Glu Ser Ser
        110             115                 120
Met Met Tyr Ala Val Ser Lys Gln Pro Ile Thr Val
                125                 130
Ala Val Ala Asp Ala Asn Ala Asn Phe Gln Tyr Tyr
            135                 140
Lys Ser Gly Val Phe Asn Gly Pro Cys Gly Thr Ser
145                 150                 155
Leu Asn His Ala Val Thr Ala Ile Gly Tyr Gly Gln
            160                 165
Asp Ser Ile Ile Tyr Pro Lys Lys Trp Gly Ala Lys
        170                 175                 180
Trp Gly Glu Ala Gly Tyr Ile Arg Met Ala Arg Asp
                185                 190
Val Ser Ser Ser Ser Gly Ile Cys Gly Ile Ala Ile
            195                 200
Asp Pro Leu Tyr Pro Thr Leu Glu Glu
    205                 210
```

Therefore, in a further aspect of the invention there is provided the use of stem bromelain protease having the amino acid sequence of SEQ ID NO 1 or a sequence substantially homologous thereto in the preparation of an agent for the treatment or prophylaxis of diarrhoea in humans.

The term "substantially homologous" would be well understood by one skilled in the art who would easily be able to determine whether or not two sequences were substantially homologous. However, in general, amino acid sequences can be described as substantially homologous when they have at least 40% homology although, for the purpose of the present invention, it is preferable for a sequence to have at least 50%, 60%, 70%, 80%, 90% or 95% homology to the amino acid sequence of SEQ ID NO 1. In addition, the residues which are compared need not be in exactly the same positions in two sequences which are substantially homologous but rather, one of the sequences may have various inserted or deleted amino acid residues or regions with respect to the sequence with which it is compared.

The invention is particularly useful in the prophylaxis, management or treatment of enterotoxigenic *E. coli* infections. However, the invention may be equally effective in addressing diarrhoea caused by other toxins, for example the toxin of *Vibrio cholerae*. It may also be effective against any diarrhoea caused by organisms that elicit a secretory process by opening of chloride channels or other channels. Moreover, bromelain would be expected to be effective against any agent being infectious or non-infectious that mediates secretion by activating signal pathways, ie by either the cAMP, cGMP or calcium-dependent pathway. Examples of agents that cause disease by activating signal pathways include the following organisms and their toxins: *Bortadella pertussis*, Salmonella species, *Campylobacter jejuni*, Pseudomonas species, Shingella species, *Yersinia enterocolitica, Klebsiella pneumoniae, Clostridium difficile* and enteropathogenic *Escherichia coli*.

To assist survival of the proteolytic enzyme through the stomach, it may be desirable to formulate the enzyme in an enteric-protected preparation. Enteric-coated tablets of bromelain are available (for example under the trademark ANANASE FORTE in the United Kingdom). Other orally administrable formulations include syrups, elixirs, and hard and soft gelatin capsules, which may also be enteric-coated.

Bromelain activity is stable over a wide pH range (pH 2–9). Therefore, it may not be necessary to enteric-protect (or enteric-coat) the bromelain or stem bromelain protease from the acid conditions in the stomach. It may, however, be necessary to protect the enzyme from digestion by acid proteases in the gut. Bromelain or stem bromelain protease may, therefore, be administered with a buffering agent, for example bicarbonate. Bromelain may be equally effective if administered alone in water or in a solution containing nutrients to assist with absorption of fluid and nutrients. Examples of suitable solutions of nutrients are those reccommended by the World Health Organisation for Oral Rehydration Therapy.

The preferred delivery system would be controlled release of the enzyme, to ensure complete removal of receptor sites along the intestine and/or exposure of all enterocytes to the protease. It would be desirable to have a combination of protection (to prevent digestion and absorption) and release all the way to the ileum.

Oral is preferred route of delivery.

Dosage of bromelain is conventionally measured in Rorer units, FIP units, BTU (bromelain tyrosine units), CDU (casein digestion units), GDU (gelatin digestion units) or MCU (milk clotting units). One Rorer unit of protease activity is defined as that amount of enzyme which hydrolyses a standardisation casein substrate at pH 7 and 25° C. so as to cause an increase in absorbence of 0.00001 per minute at 280 nm. One FIP unit of bromelain activity is contained in that amount of a standard preparation, which hydrolyses a suitable preparation of casein (FIP controlled) under the standard conditions at an initial rate such that there is liberated per minute an amount of peptide, not precipitated by a specified protein precipitation reagent, which gives the same absorbence as 1 $\mu$mol of tyrosine at 275 nm. BTUs, CDUS, GDUs and MCUs are as defined in the literature, as follows:

BTU

One bromelain tyrosine unit is that amount of enzyme which will liberate one micromole of tyrosine per minute under the conditions of the assay (for example, after digestion of an acid denatured haemoglobin substrate at pH 5 and 30° C.).

CDU

That amount of enzyme which will liberate one microgram of tyrosine after one minute digestion at 37° C. from a standard casein substrate at pH 7.0.

GDU

The enzyme activity which liberates one milligram ($10^{-3}$ g) of amino nitrogen from a standard gelatin solution after 20 minutes digestion at 45° C. and at pH 4.5.

1100 BTU/g=750 CDU/mg=1200 GDU/g.

Similar calculations can be carried out for pure stem bromelain protease. While the precise dosage will be under the control of the physician or clinician, it may be found that daily dosages of from 50 to 4000 GDU/day is appropriate, for example from 100 to 1000 GDU/day. The daily dose may be given in one or more aliquots per day, for example twice, three times or four times a day.

The invention can be used in a method for the preparation, management or treatment of diarrhoea in humans, the method comprising administering to a subject an effective amount of proteolytic enzyme.

The invention will now be described by the following examples. The examples refer to the accompanying drawings, in which:

FIG. 1 shows the effect of pure LT on rabbit ileal $I_{SC}$. Symbols represent the mean values at each time point for 4 animals. LT (2.5 $\mu$g/ml) or PBS (15 $\mu$l) was added to the mucosal bathing solution at time 0.

The arrow indicates time at which 5 mM theophylline was added to serosal bathing solution.

FIG. 2 shows the effect of bromelain on ileal $I_{SC}$. Columns represent the mean values 90–100 min after LT (2.5 $\mu$g/ml) addition, and 5 min after theophylline (5 mM) addition. Ileal tissue from 4 animals were pre-treated with bromelain (brom) for 30 minutes prior to toxin addition. Control chambers were pre-treated with bromelain plus antibody (B/Anti-B), antibody (Anti-B) or PBS alone.

FIG. 3 shows the effect of pre-treatment of ileal tissue with PBS or bromelain (15 ug/ml) on $I_{SC}$. CT (1 ug/ml) was added to the mucosal bathing solution at time 0. Number of animals tested was 9. Symbols with bars represent the mean±SE for 9 animals at selected time points. The arrow indicates the time at which 5 mM theophylline was added to the serosal bathing solution after $I_{SC}$ values reached a plateau.

FIG. 4 shows the effect of pre-treatment of ileal tissue with PBS or bromelain (15 ug/ml) on $I_{SC}$. ST (300 units) was added to the mucosal bathing solution at time 0. Number of animals tested was 6. Symbols with bars represent the mean+SE at selected time points. The arrow indicates the time at which 0.2 mM 8 bromo cGMP was added to the serosal bathing solution after $I_{SC}$ values reached a plateau.

Figure 10:
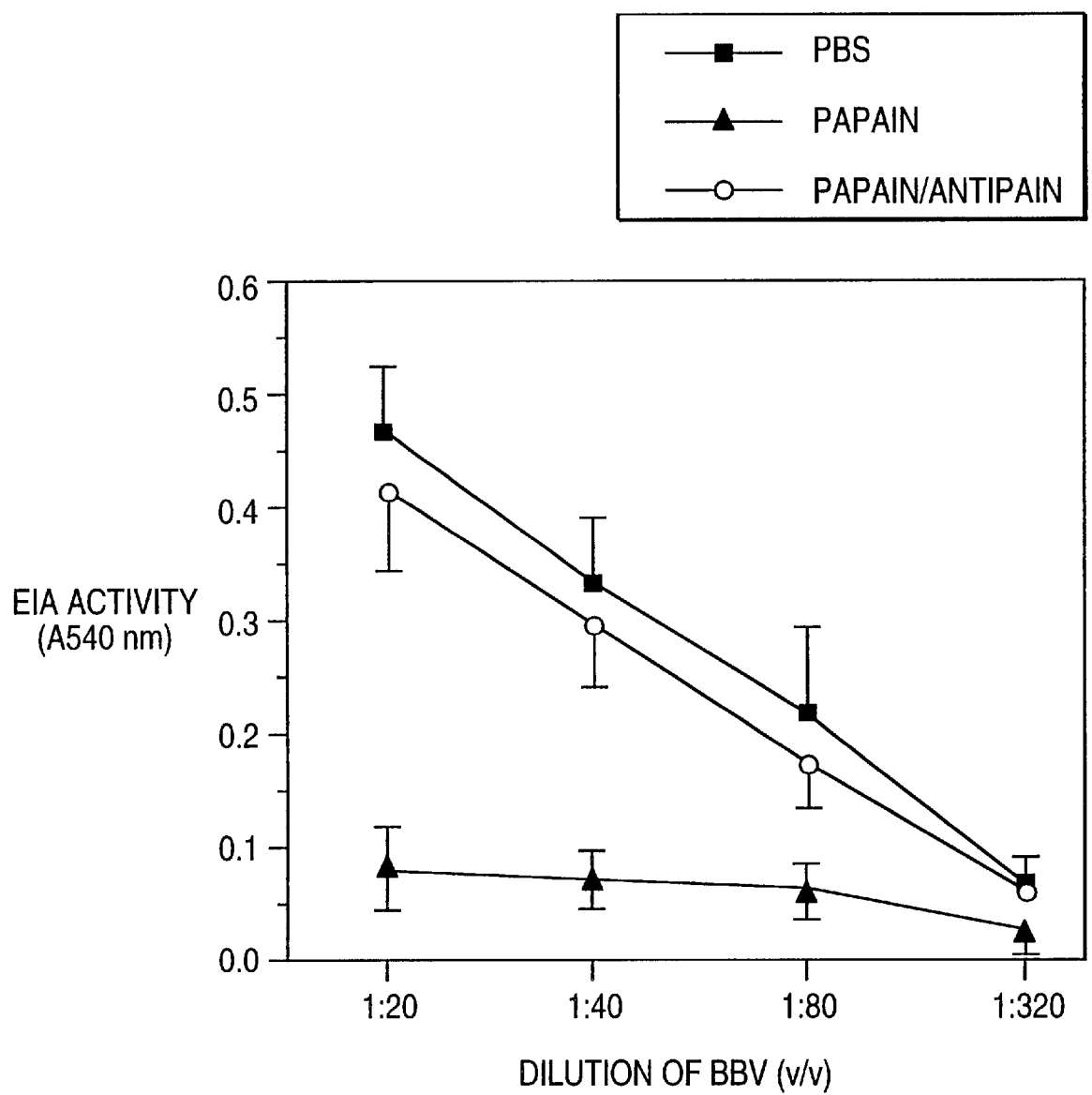

FIG. 10 shows EIA activity in relation to papain, papain plus inhibitor (Antipain) or PBS used to treat BBV coated wells. Symbols plus bars represent the mean absorbance±standard deviation of the absorbance measurements ($A_{540}$ nm) of triplicate wells tested on at least two separate occasions. BBV were pre-incubated with papain [0.0066 (w/v)], papain plus inhibitor or PBS only, prior to inoculation of wells with pure LT (1 µg/ml). Specific anti-LT IgG was diluted 1:100 in working dilution buffer.

Figure 11:
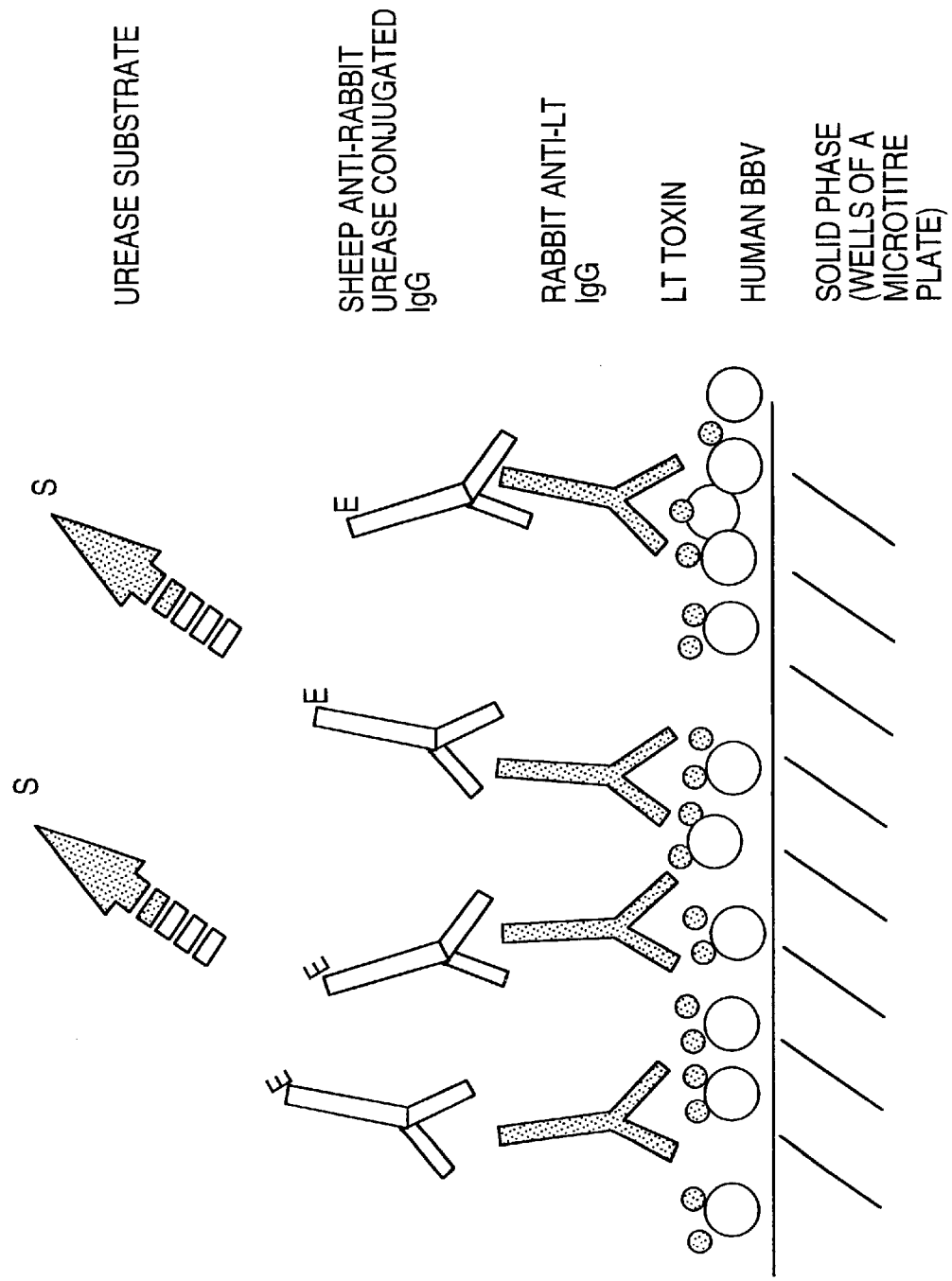

FIG. 11 shows an enzyme immunoassay (EIA) for monitoring LT toxin:brush border interaction. The EIA enabled the interaction to be studied under a wide range of reaction conditions.

Figure 12:
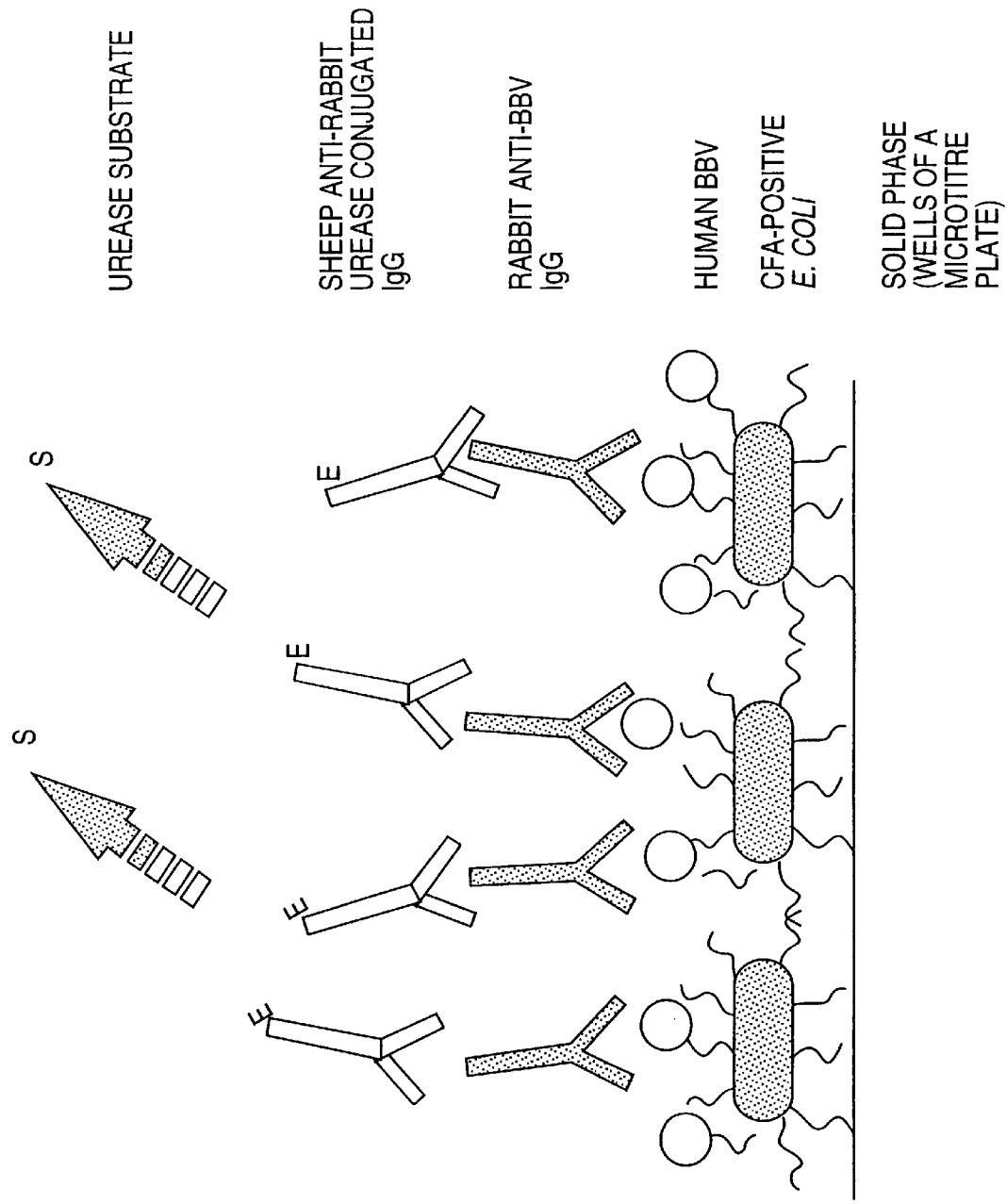

FIG. 12 shows an EIA procedure for monitoring the CFA adhesin:brush border interaction.

Figure 13:
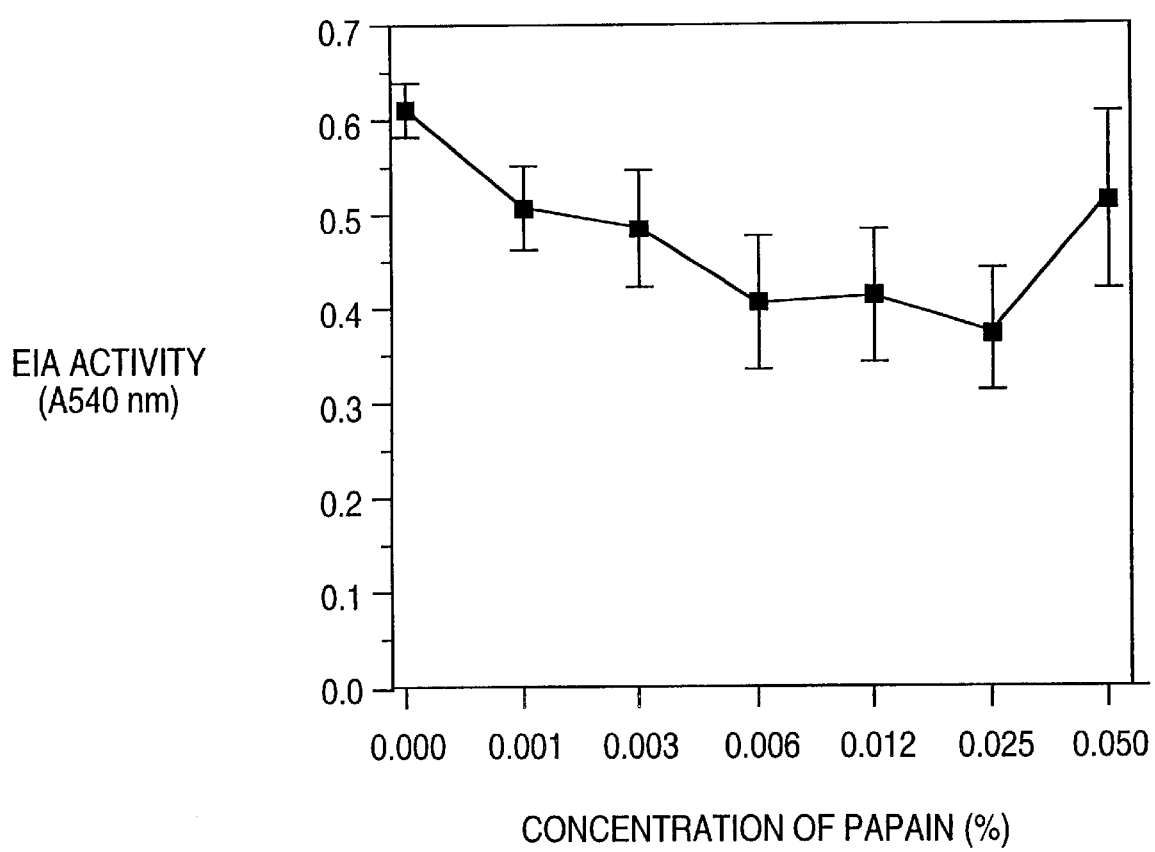

FIG. 13 shows the effect of papain treatment on the BBV coated solid phase. Symbols represent the mean absorbance of the absorbance measurements (A540 nm) of triplicate wells tested on one occasion. BBV [1:50 (v/v)] were pre-incubated with papain diluted in PBS. Anti-BBV IgG detection antibody was diluted 1:100 (v/v) in WDB.

Figure 14:
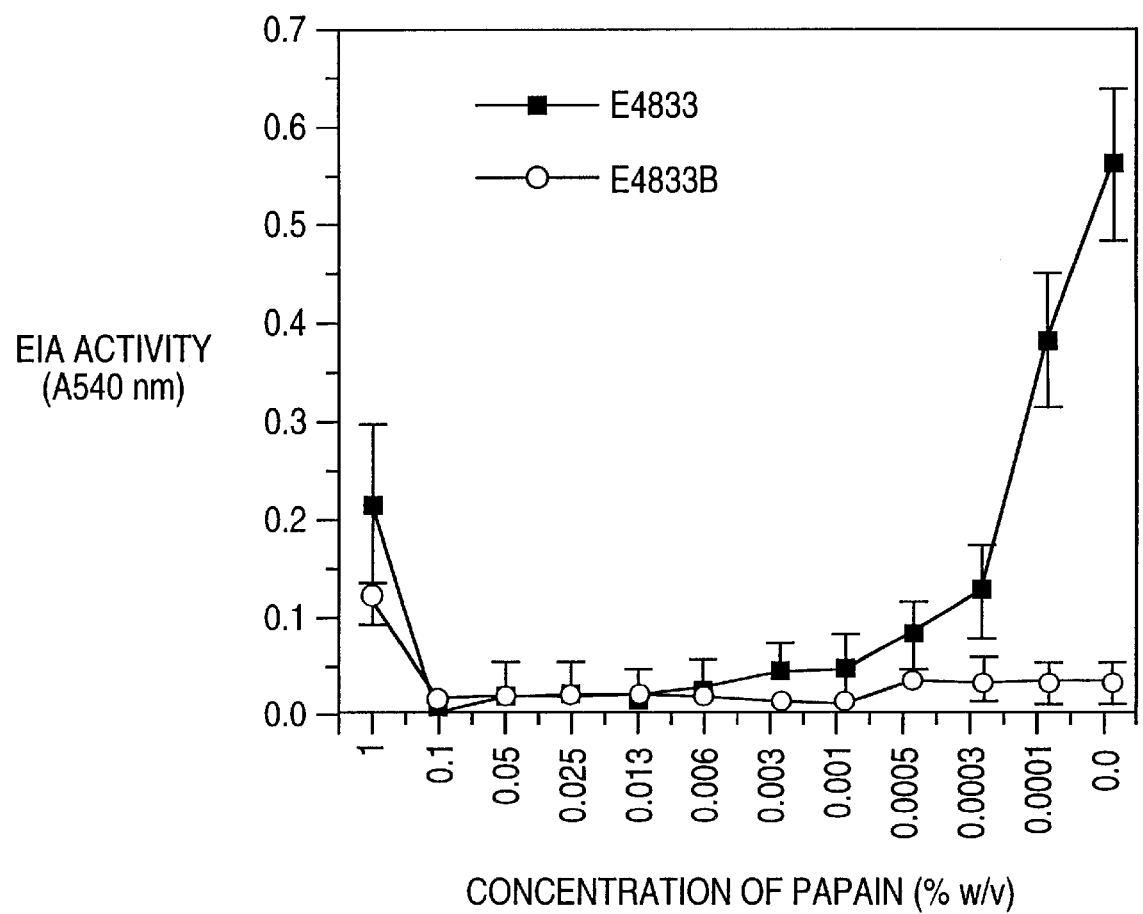

FIG. 14 shows EIA activity in relation to concentration of papain used to pre-treat BBV. Symbols represent the mean absorbance of the absorbance measurement (A540 nm) of triplicate wells tested on at least two separate occasions. BBV [1:200 (v/v)] were pre-incubated with papain prior to inclusion in E4833- or E4833B-coated wells. Anti-BBV IgG detection antibody was diluted 1:100 (v/v) in WDB.

Figure 15:
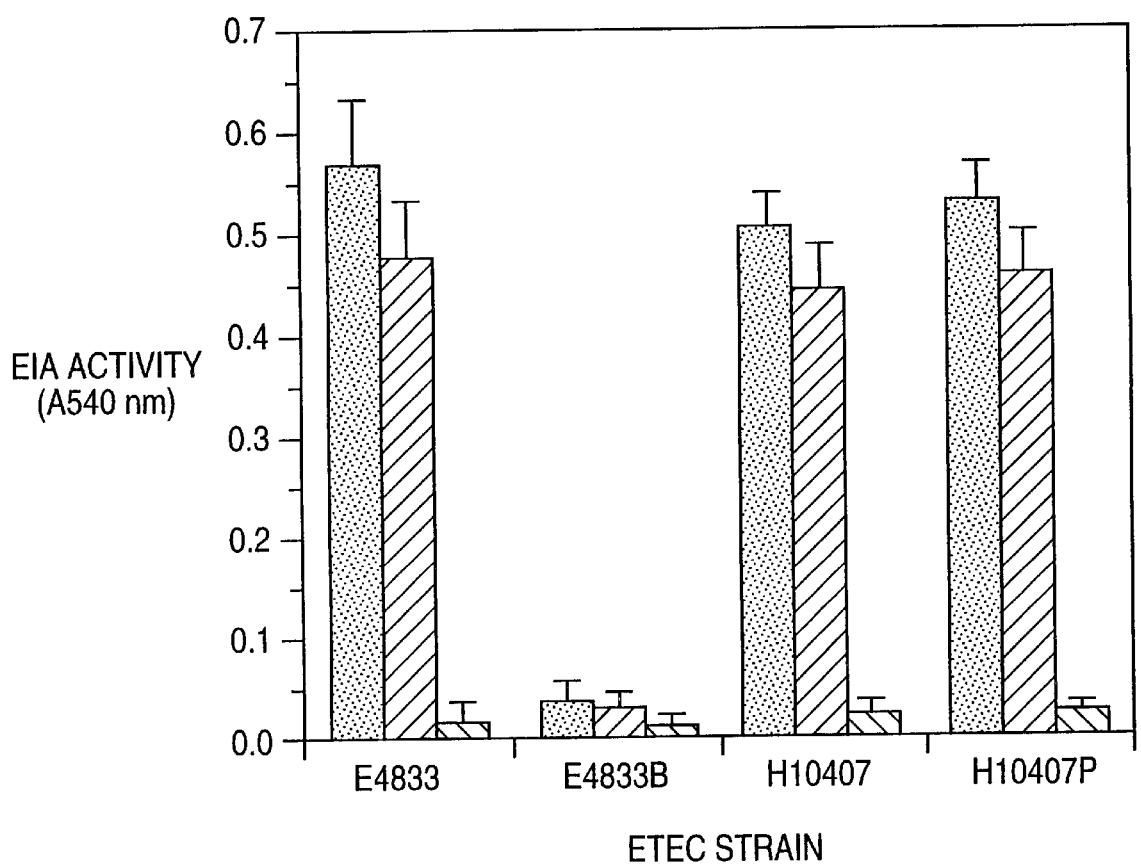

FIG. 15 shows the effect of papain on the binding of ETEC bacteria to BBV. Columns with bars represent the mean absorbance of the absorbance measurements (A540 nm) of quadruplicate wells tested on at least three separate occasions. BBV [1:200 (v/v)] were pre-incubated with papain [0.05% (w/v)], papain plus inhibitor or PBS only, prior to inclusion in bacteria coated wells. Anti-BBV IgG detection antibody was diluted 1:100 in WDB.

EXAMPLE 1

Investigation of Pre-treatment of Mucosal Tissue with Protease on LT Action in Ussing Chambers The use of rabbit intestinal tissue mounted in Ussing chambers (Ussing and Zerahn *Acta. Phys. Scandinav.* 23 110–127 (1951)) is a classical technique for studying the process of transport across intestinal tissue. The use of this ex vivo model has also proven invaluable for the study of the mechanisms of action of enterotoxins. Solutions containing CT or LT when added to the mucosal side of mounted tissue, elicit a secretory response from cells similar to that observed with perfusion of CT or LT in rabbit ileum in vivo. Addition of toxin results in an increase in transepithelial electrical potential difference (PD) and short circuit current ($I_{SC}$) of ileal mucosa by stimulation of a net anion secretory flux. This results in the serosal side becoming more positive relative to the lumenal side. The net flux of negative charge can be monitored electrochemically by means of an electrical apparatus comprising matched reference electrodes connected to a high impedance potentiometer.

Because of the usefulness of the Ussing chamber model in monitoring toxin action, the effectiveness of many anti-diarrhoeal drugs in reversing the secretory action of toxins have been tested. This example relates to experiments designed to observe the use of protease in inhibiting LT toxin secretory activity. Concurrently, the effect on the glucose-$Na^+$ active co-transport function is monitored as an indicator of tissue viability.

Experiments were performed according to Field et al, (*Am. J. Physiol.* 220 1388–1396 (1971)) with modifications described by Fasano et al, (*Proc. Natl. Acad. Sci. USA* 88 5242–5246 (1991)). Adult male New Zealand White rabbits (2–3 kg) were anaesthetised by methoxyflurane inhalation and then sacrificed by air embolism. A 15 cm segment of distal ileum was quickly excised and cut open along the mesenteric border. The ileum was then rinsed clean of luminal contents and stripped of muscular and serosal layers by means of blunt dissection. The active transport processes of the mucosa have been reported to be better maintained in stripped as opposed to unstripped ileum (Field et al, 1971 loc cit). The resulting preparation consisted of epithelium, lamina propria and muscularis mucosae. Four sections of mucosa were prepared as such from the one animal, and mounted in Lucite Ussing chambers of aperture 1.12 $cm^2$. Each surface of the tissue was continually bathed (10 ml per surface) in freshly prepared Ringers buffer containing NaCl (53 mM), KCl (5 mM), $Na_2SO_4$ (30.5 mM), mannitol (30.5 mM), $Na_2HPO_4$ (1 69 mM), $NaH_2PO_4$ (0.3 mM), $CaCl_2$ (1.25 mM), $MgCl_2$ (1.1 mM) and $NaHCO_3$ (25 mM). The bathing solution was maintained at 37° C. with water-jacketed reservoirs connected to a constant-temperature circulating pump and gassed with 95% $O_2$/5% $CO_2$.

The PD (the difference in voltage measured on the mucosal side versus the serosal side of the tissue) and $I_{SC}$ (the amount of current needed to nullify the PD) were then measured as previously described (Field et al, 1971 loc cit). A positive PD indicated that the serosal potential was higher than the luminal potential, that is the net flux from the mucosa (M) to serosa (S) was positive. The tissue resistance (R) for each animal was also calculated from Ohm's Law where $I_{SC}$=PD/R, so that results between individual animals could be compared. Prior to mounting the tissue, the fluid resistance ($R_f$) was determined and incorporated into the calculations. Once the tissue was mounted and prior to experimentation, the $I_{SC}$ was determined at approximately 10 min. intervals until the tissue reached a steady state. Four sections of tissue from the same animal were mounted simultaneously and used for each experiment. To test for leakiness of the system owing to perforations of the ileal tissue, 200 µl of 0.5 mM solution of glucose and mannitol diluted in Ringers was added to the serosal and mucosal side respectively prior to experimentation.

Once the tissue reached equilibrium (time 0), the test material (0–100 µl) was added to the mucosal side. The same volume of sample was added to the serosal side to preserve osmotic balance. Variations in $I_{SC}$, PD and R were then recorded every 5–10 mins. At the end of every experiment, 200 µl of 0.5M glucose was added to the mucosal side of each chamber. Only those tissues that showed an increase in $I_{SC}$ in response to glucose (indicating tissue viability) were included in the analysis. The increase in $I_{SC}$ upon glucose addition is due to enhancement of $Na^+$ absorption mediated by the electrogenic coupled transfer of $Na^+$ with glucose into the cell.

Pieces of rabbit ileum exposed to a range of concentrations of bromelain (0–1000 µg/ml) for 30 min were examined by light microscopy and electron microscopy. Tissue exposed to PBS alone was used for comparison.

For light microscopy, tissue was fixed in neutral buffered formalin and stained with haematoxylin/eosin and tissue gram stain. Tissues for electron microscopy were fixed in 3% (v/v) glutaraldehyde/0.1M sodium cacodylate buffer (pH 7.4) and then stored at 4° C. until required.

1a Light Microscopy

At examination of the tissues, particular attention was directed to morphological and structural changes in both the intestinal villi and the brush border lining.

Tissue samples exposed to 1000 µg/ml of bromelain did not respond to glucose addition at the end of the treatment period, indicating that the tissue was no longer viable. Light microscopic examination of these samples revealed pronounced marked vacuolar degeneration. The villus structure was absent and there was coagulation necrosis of individual epithelial cells lining the remnants of the villus.

The ileal tissue that was treated with 50 μg/ml of bromelain was viable after glucose addition; however, the $I_{SC}$ response was not maximal, indicating some necrosis of the tissue. Light microscopy confirmed this observation, whereby samples exhibited some coagulation necrosis of luminal epithelial cells and vacuolar degeneration, indicating dead or dying cells. The villus architecture of these tissue preparations, however, remained intact.

Tissue treated with 10 μg/ml of bromelain had an intact mucosa with villi lined by tall columnar epithelium. In general the tissue appeared normal, yet occasional cells showed some coagulation necrosis. There was a large response to glucose addition after 30 minutes of bromelain treatment, indicating healthy, viable tissue. The occasional cells that may have been affected by bromelain treatment, therefore did not appear to adversely affect the absorptive capacity of the tissue.

1b Electron Microscopy

Examination of tissue treated with 10 μg/ml of bromelain by transmission electron microscopy revealed no morphological changes to the microvilli. The glycocalyx or mucus overlay was seen to be intact.

1c Effect of LT on $I_{SC}$ Across Ileal Mucosa

Figure 1:
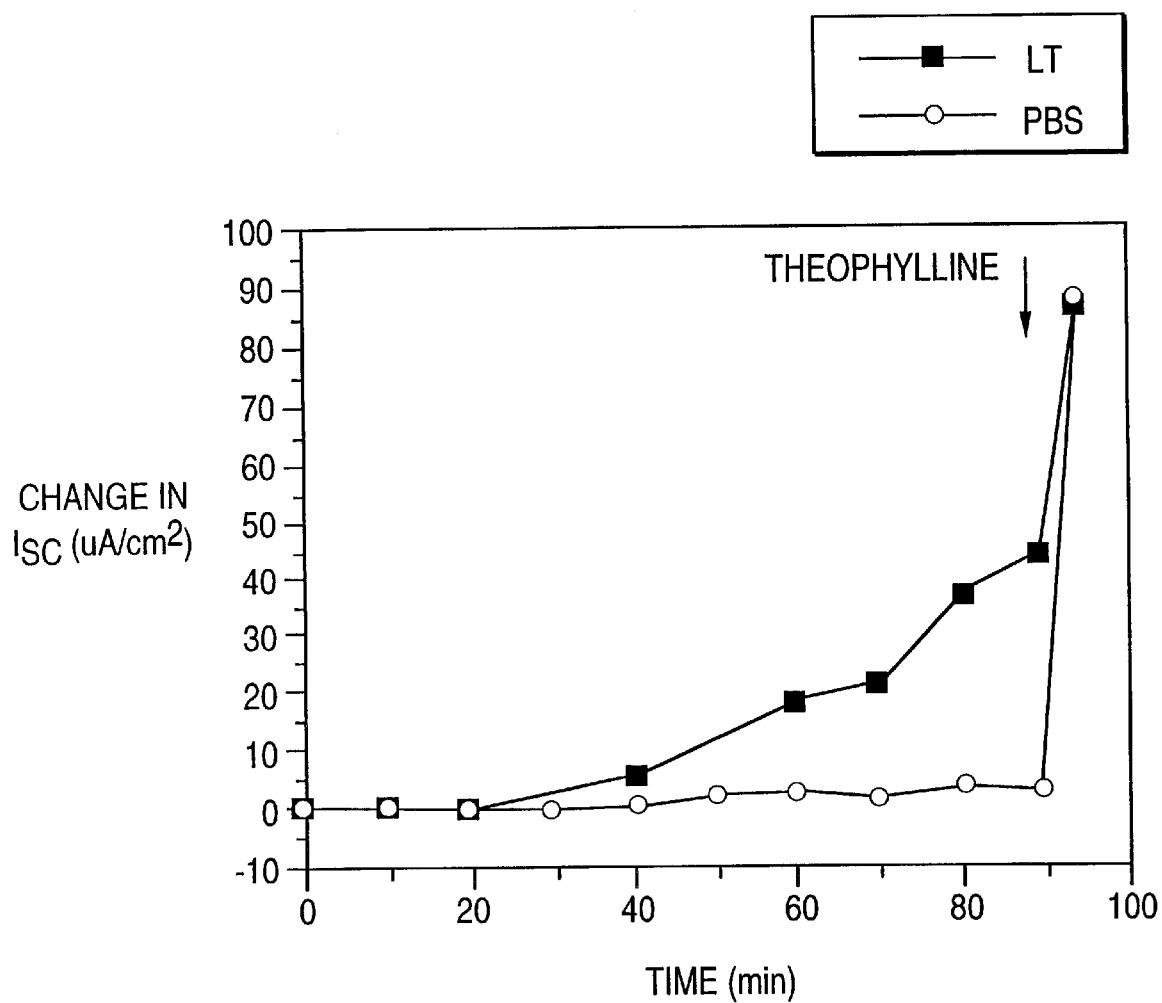

The changes in $I_{SC}$ produced by addition of 25 μg of pure LT (final concentration was 2.5 μg/ml) to the luminal side of the ileal mucosa are shown in FIG. 1. the $I_{SC}$ began to increase 40–50 min after addition of toxin. In chambers where tissue was exposed to PBS only, there was a negligible change in $I_{SC}$. Studies have shown that 40–60 min after CT addition there is a gradual progression to a maximal effect which occurred over the next few hours. Continuation of this effect occurred despite removal of all free toxin. Toxin that had been heat treated prior to exposure to the tissue had no effect. In addition, toxin exposed to the serosal side of the tissue had no effect on $I_{SC}$ indicating that action only occurred after binding to receptors located on the brush border membrane.

Theophylline, a methylxanthine, was added to the serosal side of the tissue to observe the change in $I_{SC}$ due to cAMP. Theophylline inhibits cyclic nucleotide phosphodiesterases and thus elevates cAMP by inhibiting the conversion of AMP to 5'-AMP. The effects of theophylline, cAMP alone and saturable amounts of CT on Na and Cl fluxes are the same. The effects of theophylline on flux, however, occur after only a few minutes.

Addition of theophylline (final concentration 5 mM) to the serosal side of the toxin-treated tissue resulted in a further increase in $I_{SC}$. The increase in $I_{SC}$ due to theophylline on PBS treated mucosa was equivalent to the final $I_{SC}$ due to the combined toxin and theophylline treatment. This indicates that the change in $I_{SC}$ due to LT addition was due to the toxin action on cAMP and not by any other mechanism. The same change in $I_{SC}$ also showed that the amount of toxin and hence its activity used in this experiment was not maximal. That is, more toxin was required to occupy all receptors in order to exhibit maximal levels of cAMP and hence $I_{SC}$.

At the completion of the experiment, glucose was added to the lumenal side of the chamber. This resulted in a further increase in $I_{SC}$ indicating that the tissue was viable.

1d Effect of Bromelain on Secretory Effect caused by *Escherichia coli* heat-labile Toxin (LT)

Bromelain diluted in PBS (final concentration 10 μg/ml) was added to both the mucosal and serosal side of the tissue. Control chambers were included whereby bromelain (100 μg/10 μl) was first pre-incubated (30 min at 37° C.) with an equal volume of an anti-bromelain antibody (IgG) (0.5 mg/ml) prior to addition to the chamber. Other chambers contained antibody or PBS alone. All chambers were then allowed to incubate for 30 min to enable sufficient bromelain pre-treatment of the mucosal tissue. Prior to addition of toxin the chambers were completely emptied of Ringers (see above) and rinsed twice to ensure complete removal of antibody and bromelain. The chambers were then re-filled with fresh Ringers and the tissue allowed to stabilise. LT (2.5 μg/ml) was then added to the mucosal side and the experiment completed as described above.

Figure 2:
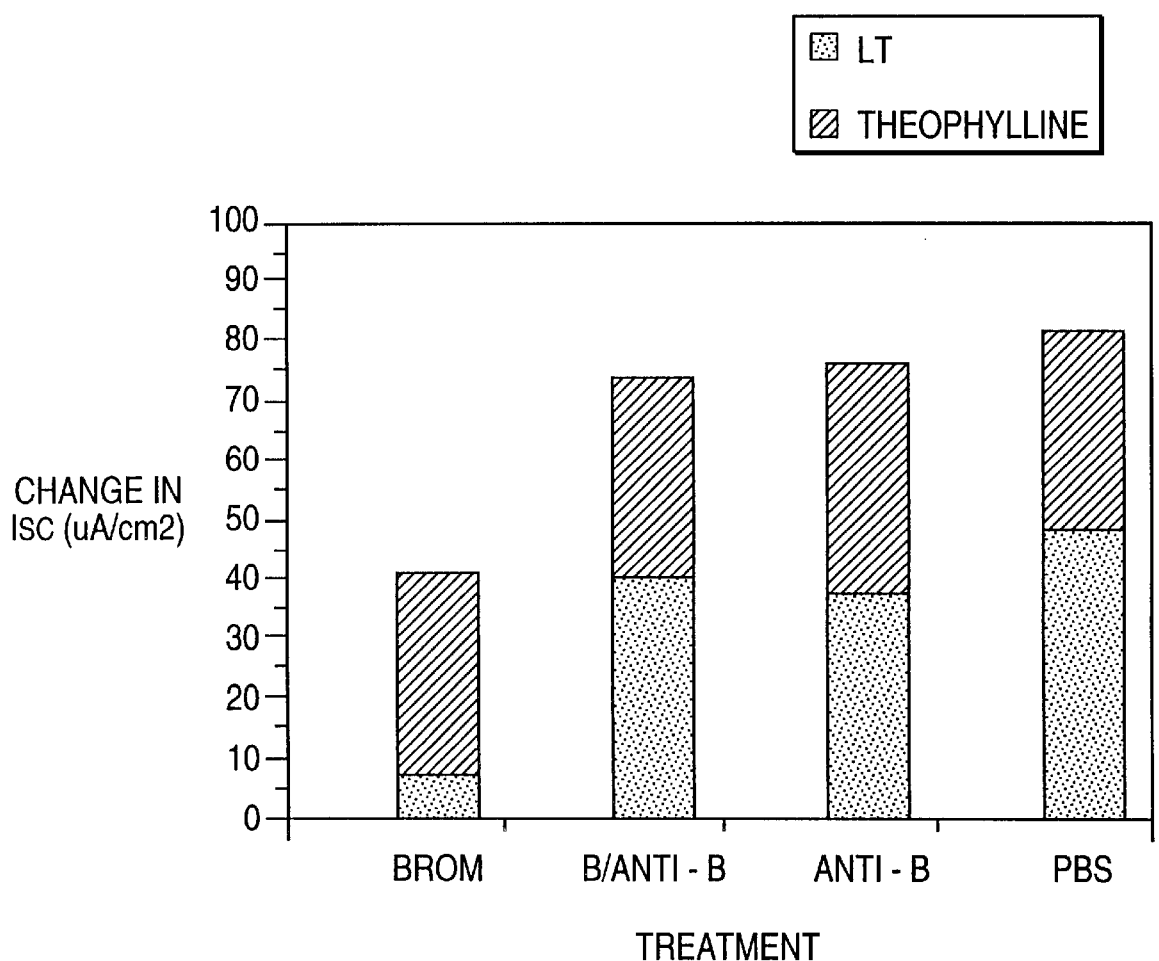

FIG. 2 shows the change in $I_{SC}$ produced by pre-treatment of tissue with bromelain or control substance prior to addition of LT. In all control chambers, the $I_{SC}$ began to increase 40–50 min after addition of toxin as observed above. This result indicates that the anti-bromelain IgG and bromelain pre-incubated with antibody had no effect on the LT action. It also shows that changing the Ringers buffer had no effect on the tissue.

In chambers that were pre-treated with bromelain, there was no change in $I_{SC}$ after 60 min, indicating that the bromelain had completely inhibited the secretory effect of LT. Addition of theophylline to control chambers, showed a further increase in $I_{SC}$ of 40% to 50%. In comparison, addition of theophylline to the bromelain treated chamber only showed a similar increase in $I_{SC}$. The final change in $I_{SC}$ was therefore 40% to 50% less than that of the combined effect of LT and theophylline in control chambers. It is presumed that some other mechanism of action of bromelain in inhibiting fluid secretion may be present. Bromelain has been reported to inhibit the synthesis of prostaglandins, which are known to inhibit cAMP production (Taussig and Batkin, 1988). Other molecules that inhibit the synthesis of prostaglandins, including aspirin, indomethacin and ibuprofen, have also been shown to inhibit intestinal fluid secretion induced by bacterial toxins (Gots et al, 1974; Finch and Katz, 1972; Peterson et al, 1988).

These data indicate that the bromelain had completely inhibited the net anion flux of Cl⁻ and hence secretagogue effect of LT. The data also indicate that bromelain has an additional mechanism for inhibiting fluid secretion, other than its ability to inhibit binding of toxin to intestinal receptors. The observation that total $I_{SC}$ levels in bromelain-treated tissue combined with prostaglandin (see Example 2b) or theophylline failed to reach the same levels as control tissues, supports this hypothesis.

Addition of glucose at the end of the experiment showed a further increase in $I_{SC}$, therefore indicating that glucose-Na⁺ transport was unaffected. Because the enhancement of Na absorption did not appear to be substantially effected by pre-treatment of tissue with protease, the implication is that bromelain does not result in extensive physiological damage to the mucosa. This result is confirmed by the light microscopy study, referred to above and by influx studies described in Example 7b.

EXAMPLE 2

Investigation of Pre-treatment of Mucosal Tissue with Protease on CT Action in Ussing Chambers 2a Effect of bromelain on secretory effect caused by cholera toxin (CT)

In a similar experiment to that described in Example 1d, bromelain diluted in PBS (final concentration 15 ug/ml) was added to both the mucosal and serosal side of the ileal tissue. Control tissues were treated with PBS alone. Chambers were allowed to incubate for 30 minutes and rinsed as described above. CT (10 ug) was then added to the mucosal side and the experiment completed as before.

Figure 3:
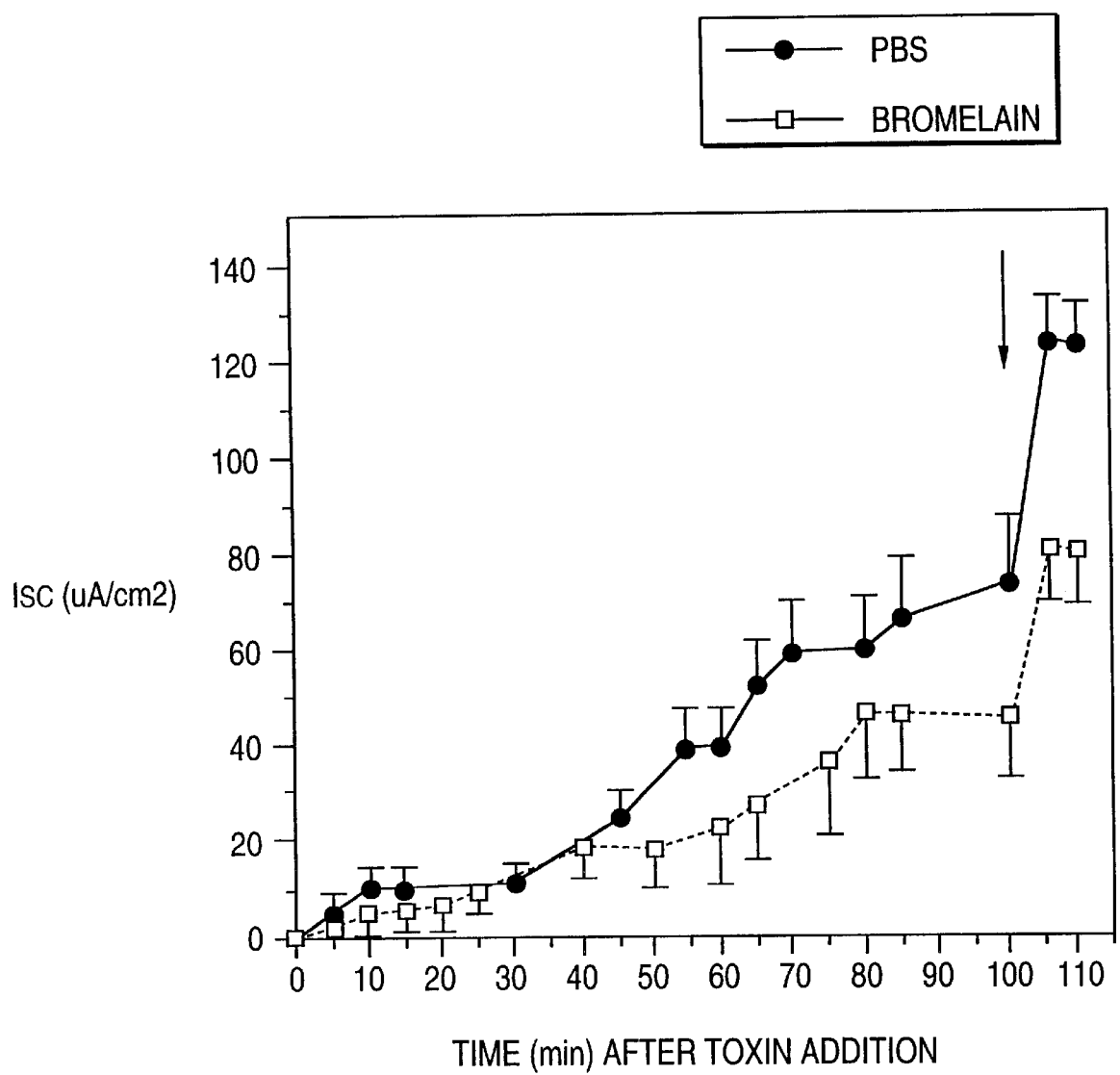

FIG. 3 shows the change in $I_{SC}$ produced by pre-treatment of tissue with PBS or bromelain. The data shows that bromelain reduced the change in $I_{SC}$ and PD and therefore the secretory effect caused by CT. The reduction in $I_{SC}$ and PD values induced by bromelain was 60% (p=0.001) and 70% (p=0.002) respectively. See Table 1 of Ussing chamber data.

allowed to incubate for 30 minutes and rinsed as described above. ST (300 units) was then added to the mucosal side and the experiment completed as before.

Figure 4:
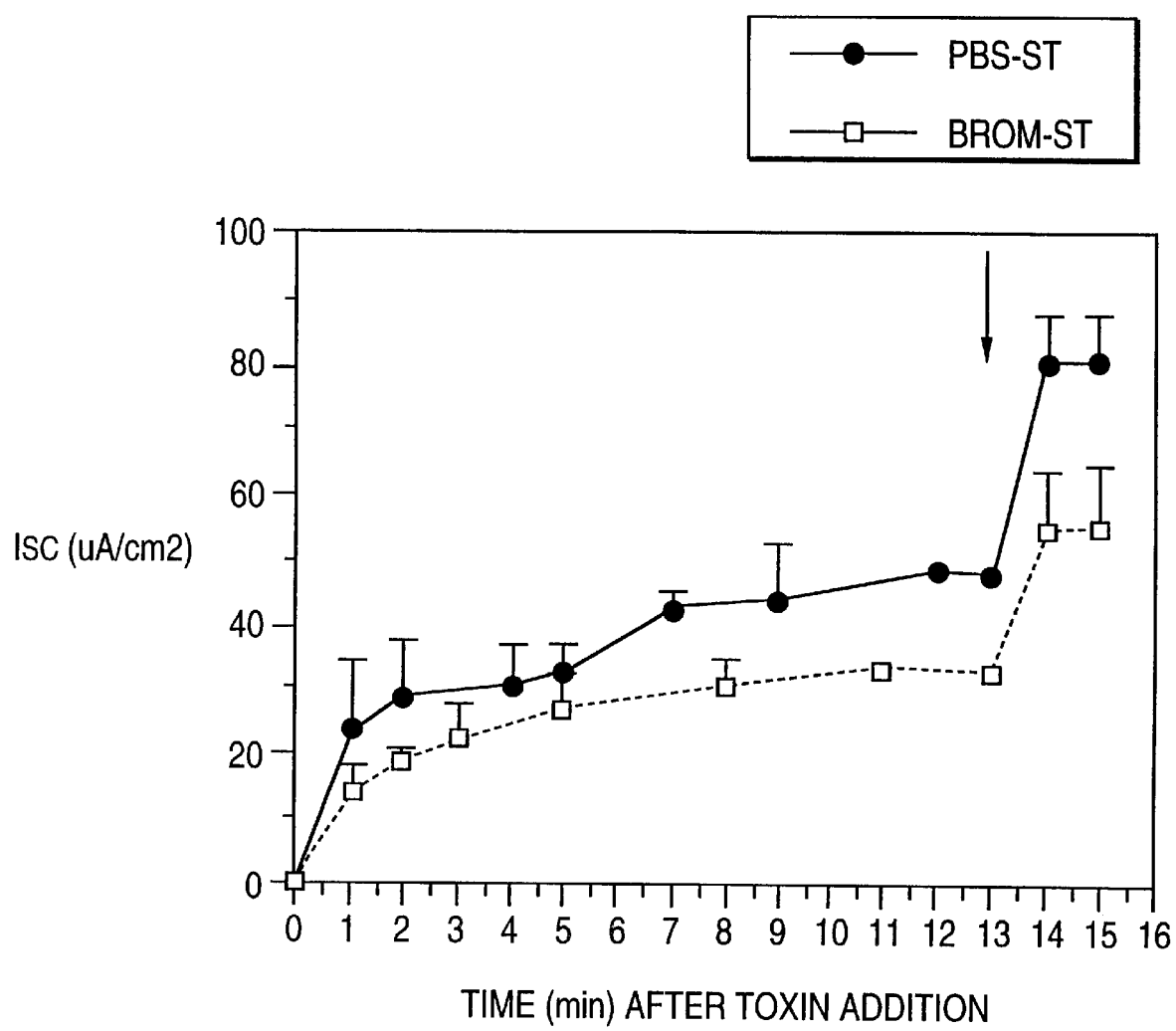

FIG. 4 shows the change in $I_{SC}$ produced by pre-treatment of tissue with PBS or bromelain. The data show that bromelain reduced the change in $I_{SC}$ and PD and therefore the secretory effect caused by ST. The reduction in $I_{SC}$ and PD values induced by bromelain was 34% (p=0.0313) and 33% (p=0.06) respectively and this is shown in Table 1.

TABLE 1

Effect of bromelain treatment of ileal tissue on Δ $I_{sc}$ and PD

| Toxin | n | Δ $I_{sc}$ ($\mu A/cm^2$) | | | Δ PD (mV) | | |
|---|---|---|---|---|---|---|---|
| | | PBS | Bromelain | P | PBS | Bromelain | P |
| LT | 7 | 52.0 ± 7.3 | 13.4 ± 5.2 | 0.02 | 1.1 ± 0.2 | 0.3 ± 0.2 | 0.03 |
| + theo | 7 | 90.6 ± 10.2 | 45.8 ± 8.5 | 0.03 | 2.2 ± 0.3 | 1.0 ± 0.3 | 0.01 |
| CT | 9 | 58.5 ± 8.3 | 25.7 ± 6.9 | 0.001 | 1.2 ± 0.1 | 0.4 ± 0.2 | 0.002 |
| + theo | 6 | 107.4 ± 15.0 | 62.5 ± 12.8 | 0.01 | 2.3 ± 0.4 | 1.5 ± 0.4 | 0.01 |
| + $PGE_2$ | 4 | 93.2 ± 11.1 | 49.1 ± 10.6 | 0.02 | 2.5 ± 0.2 | 0.9 ± 0.2 | 0.02 |
| ST | 6 | 45.0 ± 2.8 | 29.4 ± 4.3 | 0.03 | 1.6 ± 0.2 | 1.0 ± 0.1 | 0.06 |
| + 8-Br-cGMP | 6 | 80.1 ± 5.3 | 55.2 ± 6.4 | 0.002 | 2.6 ± 0.2 | 1.7 ± 0.1 | 0.01 |

Data and means ± SE for n animals.
P refers to significance of differences (paired t-test) between bromelain-treated and control tissues when $I_{sc}$ and PD responses are maximal.
$PGE_2$, prostaglandin $E_2$; theo, theophylline; 8-Br-cGMP, 8-Bromo-CGMP.

Theophylline was added to the serosal side of the tissue when $I_{SC}$ and PD values reached a plateau, indicating maximal effect of the toxin. Addition of theophylline at the end of the experiment showed similar increases in $I_{SC}$ and PD in both the bromelain-treated and PBS-treated tissue, as observed previously in LT experiments described in Example 1. This resulted in a final reduction in total $I_{SC}$ and PD of 44% (combined effect of toxin and theophylline) in tissues treated with bromelain as compared to control tissues (Table 1). This observation suggests that another mechanism for inhibiting fluid secretion exists.

2b Effect of Prostaglandin E2 (PE2) on $I_{SC}$ in bromelain treated tissue

To observe whether the reduction in total $I_{SC}$ levels in bromelain treated tissue was because of reduced intracellular levels of cAMP as a result of reduced prostaglandin levels, exogenous prostaglandin was added to the serosal side of the chamber when $I_{SC}$ and PD values had reached a plateau. PE2 ($1\times10^5$M) was added instead of theophylline. The data presented in Table 1 of Ussing chamber data, indicate that there is still a reduction of 48% and 64% respectively, in the total $I_{SC}$ and PD in bromelain and CT treated tissue, compared with the combined effect of CT and PE2 in control (PBS treated) chambers.

These data suggest the additional mechanism by which bromelain reduces fluid secretion cannot be completely explained by its reported ability to inhibit the synthesis of prostaglandins.

EXAMPLE 3

Effect of Bromelain on secretory effect due to
*Escherichia coli* heat stable toxin (ST)

Experiments were conducted in a similar manner as for those using LT (Example 1d) and CT (Example 2a). Bromelain diluted in PBS (final concentration 15 ug/ml) was added to both the mucosal and serosal side of the ileal tissue. Control tissues were treated with PBS alone. Chambers were 8-Bromoguanosine 3' 5'-cyclic monophosphate (final concentration 0.2 mM), an analogue of cGMP known to simulate cGMP production, was added to the serosal side of the tissue when PD and $I_{SC}$ values had reached a plateau (maximal response because of ST). Similar additional increases in $I_{SC}$ and PD in both the bromelain-treated and PBS-treated tissue were noted as a result of cGMP addition, with the final total $I_{SC}$ and PD values in bromelain-treated tissues being significantly less than that of control tissues. This is shown in FIG. 4 and also in Table 1.

Significant reductions in total PD and $I_{SC}$ values was observed as in earlier experiments when tissue was treated with bromelain prior to the addition of CT or LT. The final combined $I_{SC}$ and PD values of control tissues treated with toxin followed by addition of theophylline or PE2, was significantly higher than that of bromelain pre-treated tissues.

It is hypothesised that bromelain has an additional mechanism for inhibiting fluid secretion, other than inhibiting the ability of toxin to bind to intestinal receptors. If bromelain were to only prevent the attachment of toxin to the intestinal cells, all intracellular biochemical pathways would remain unaffected. The observation that total $I_{SC}$ and PD levels in bromelain-treated tissue fail to reach the same levels as PBS-treated tissue after addition of a second messenger (ie 8-Br-cGMP, PE2 or theophylline), implies that bromelain does affect an internal signals within cells. The ability of bromelain to reduce the total $I_{SC}$ and PD changes induced by 8-Br-cGMP, implies an effect after cyclic nucleotide generation. Other molecules affect intracellular processes, for example chlorpromazine and indomethacin, however these molecules appear to be active only against submaximal doses of toxin (ST). Furthermore, these molecules have been found to be unsuitable for clinical use against diarrhoea because of undesirable side effects. Bromelain, in contrast, is effective against maximal doses of toxin and has been shown to be clinically safe.

All of the experiments described above indicate that bromelain is effective in inhibiting secretion induced by bacterial enterotoxins and also by inhibiting secretion induced by bacterial toxins combined with other secretagogues (second messengers for internal signals).

The next series of examples (Example 4 to Example 7) describe the ability of bromelain and stem bromelain to inhibit the secretion induced by second messengers alone, without the addition of bacterial toxin. Examples also demonstrate that bromelain can inhibit secretion induced by endogenous mediators of secretion (i.e. that induced by hormones or neurotransmitters or nutrients).

EXAMPLE 4

Effect of Crude Bromelain and Pure Stem Bromelain Protease on Secretion Induced by Cyclic Nucleotides Experiments were conducted in a similar manner as for those described in Examples 1 to 3, with the exception that no bacterial toxins were used in these experiments. Bromelain or stem bromelain diluted in PBS (final concentration 15 ug/ml) were added to both sides of the ileal tissue. Control tissues were treated with PBS alone. Chambers were allowed to incubate for 30 minutes and rinsed as described above. Analogues of cAMP and cGMP (8-Bromo-cAMP and 8-Bromo-cGMP; 0.2 mlM) were added to the serosal side of the tissue. These analogues induce secretion by stimulating increased levels of these cyclic nucleotides.

Figure 5A:
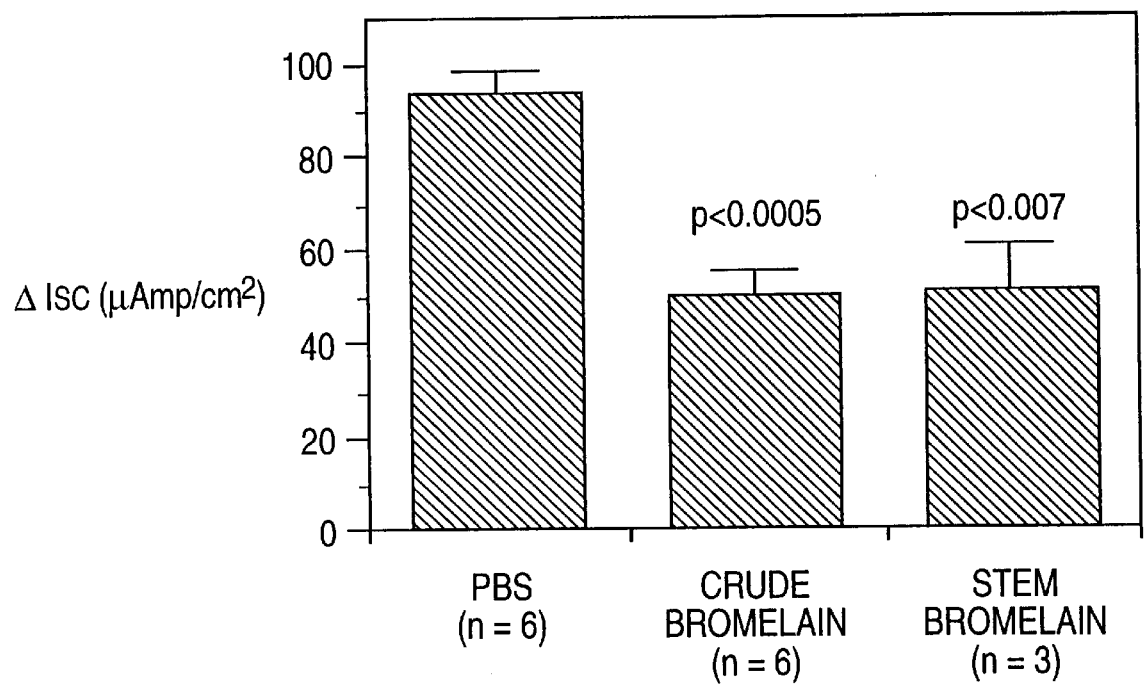
FIG. 5 shows the effect of pre-treatment of ileal tissue with PBS, stem bromelain protease and bromelain on $I_{SC}$ and PD changes caused by 8-bromo-cAMP. (p values reveal significance as determined by paired t-test).
Figure 5B:
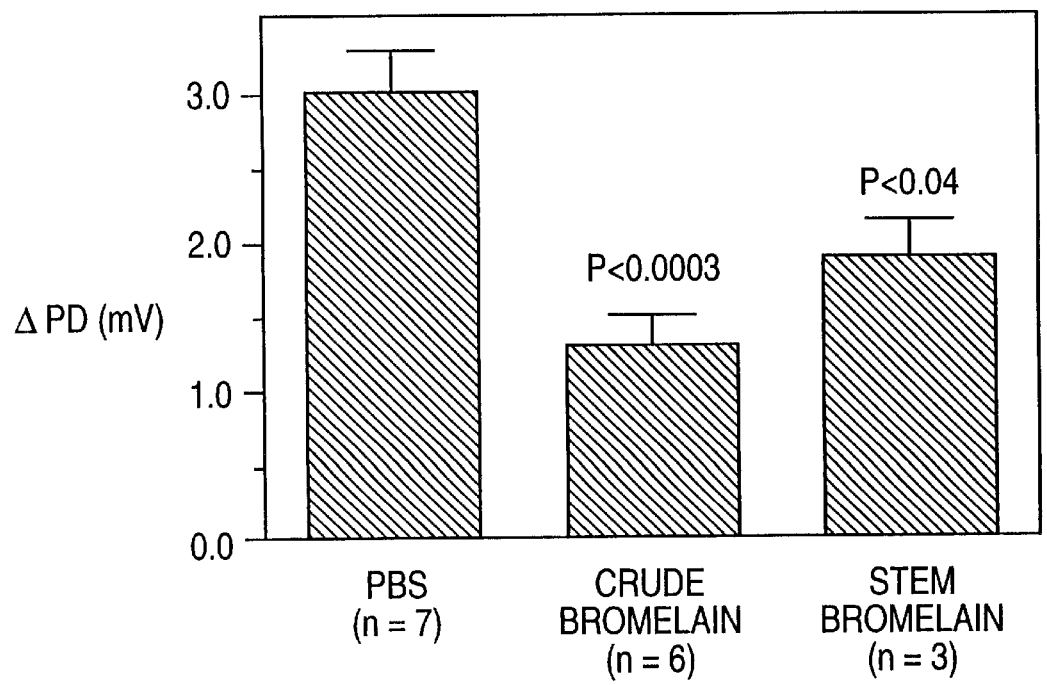
Figure 6A:
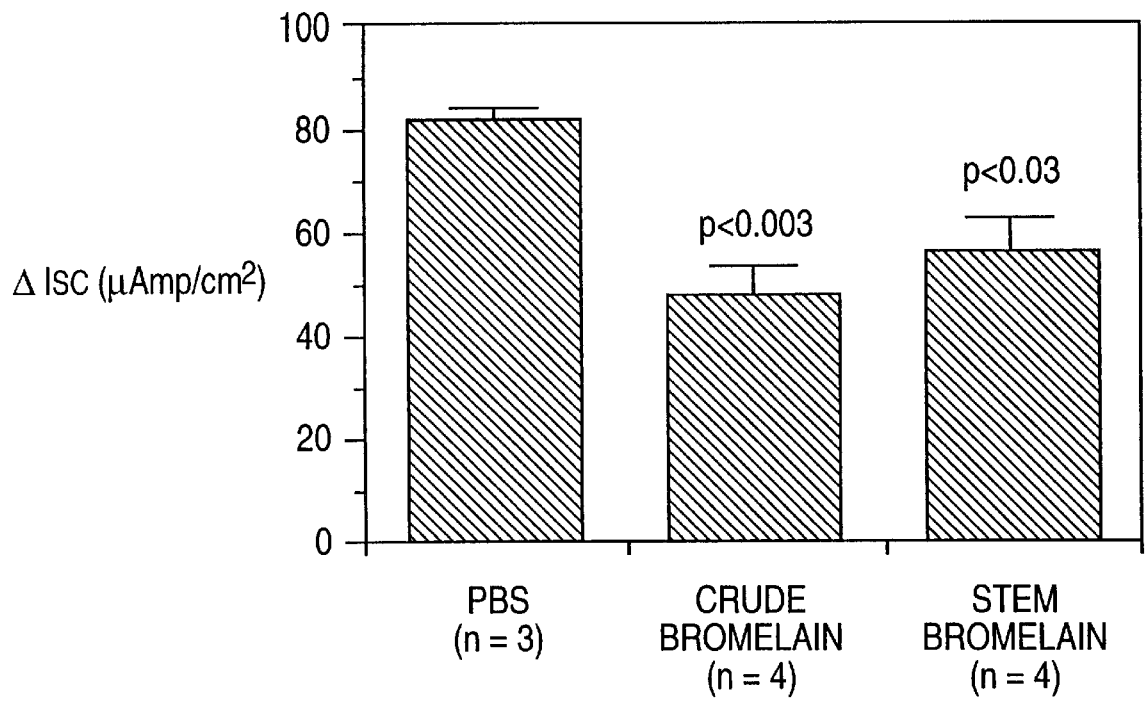
FIG. 6 shows the effect of pre-treatment of ileal tissue with PBS, stem bromelain protease and bromelain on $I_{SC}$ and PD changes caused by 8-bromo-cGMP. (p values reveal significance as determined by paired t-test).
Figure 6B:
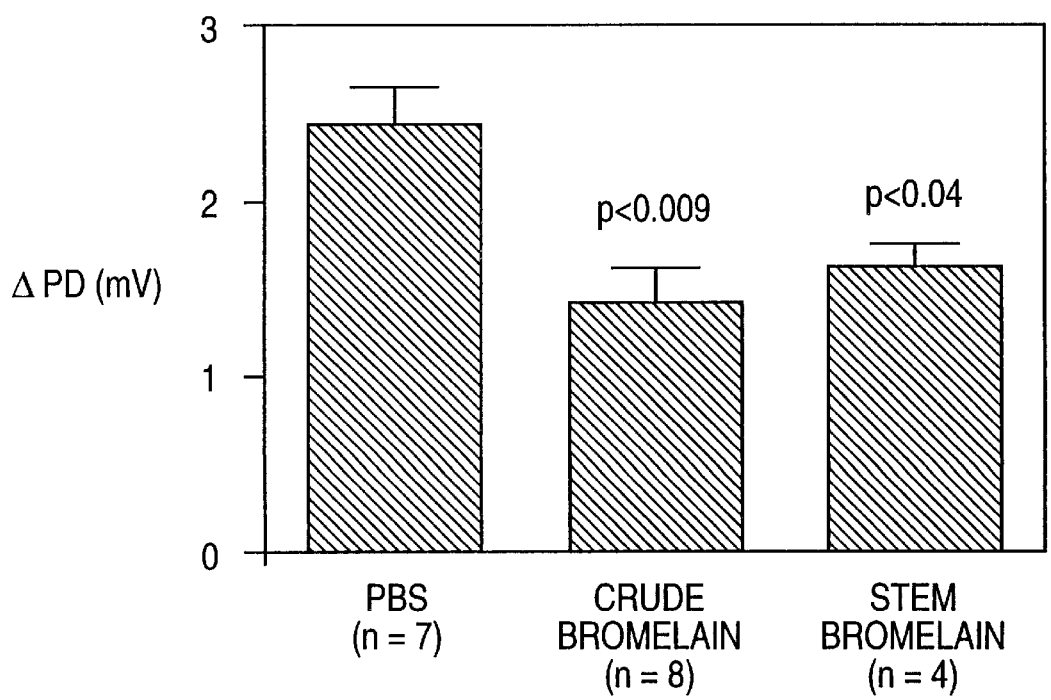

FIG. 5 and FIG. 6 show the change in $I_{SC}$ and PD produced by pre-treatment of tissue with either PBS, bromelain or stem bromelain. The data show that bromelain and stem bromelain were equally effective in reducing the PD and $I_{SC}$ and therefore secretion induced by both 8-Bromo-cAMP and 8-Bromo-cGMP.

The data presented demonstrate that bromelain and stem bromelain are effective in inhibiting secretion caused by increased intracellular levels of cyclic nucleotides. This finding suggests that stem bromelain protease is responsible for the anti-diarrhoea action of bromelain.

EXAMPLE 5

Effect of Bromelain on Secretion caused by theophylline and Prostaglandin E2

Experiments were conducted in a similar manner as for those described in Example 4. Bromelain diluted in PBS (final concentration 15 ug/ml) were added to both sides of the ileal tissue. Control tissues were treated with PBS alone. Chambers were allowed to incubate for 30 minutes and rinsed as described above. Theophylline (9 mg) or prostaglandin E2 ($1\times10^{-5}$M) was added to the serosal side of the tissue. These molecules stimulate secretion by action on the cAMP pathway.

Figure 7:
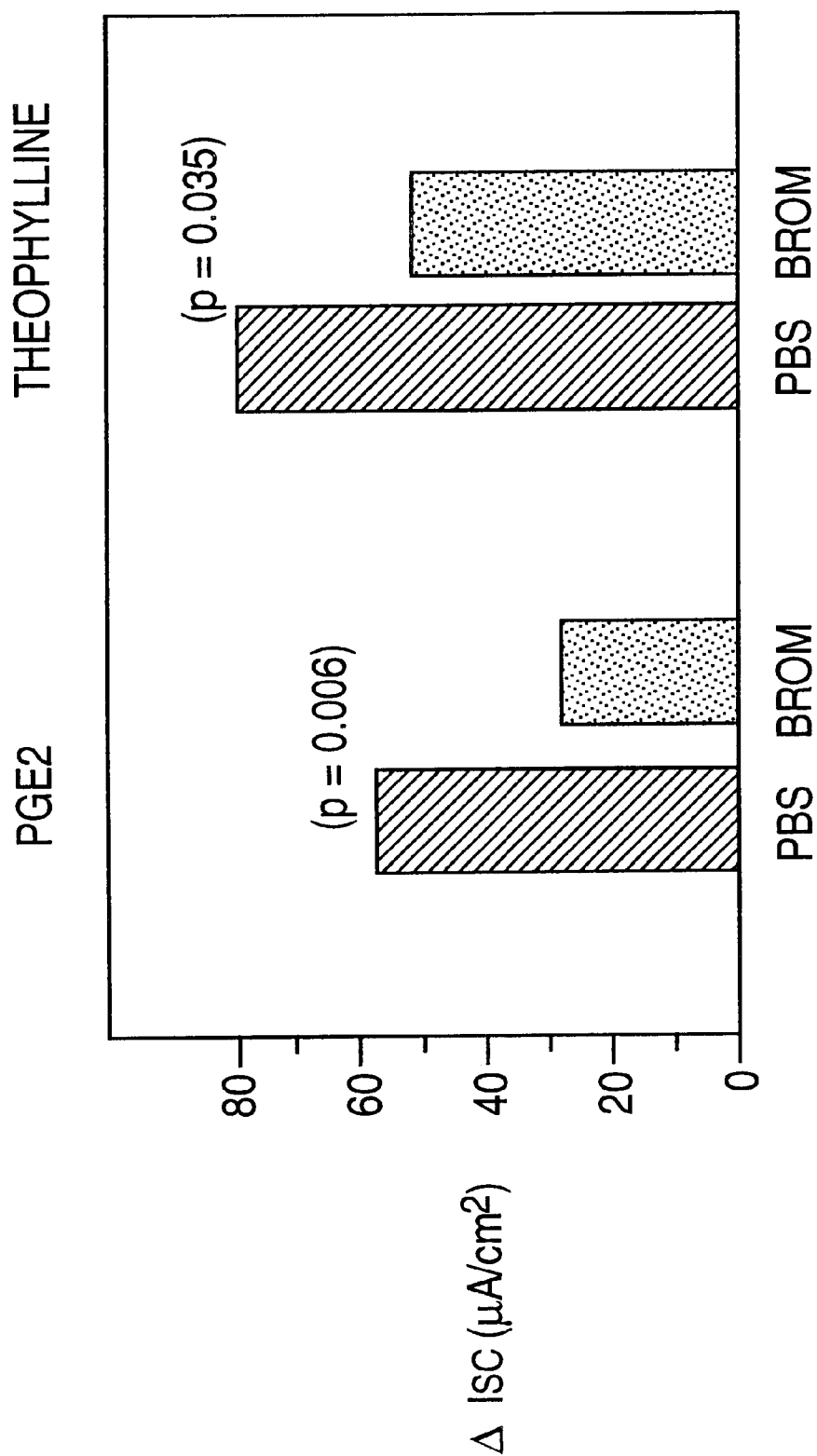
FIG. 7 shows the effect of pre-treatment of ileal tissue with PBS or bromelain on $I_{SC}$ changes caused by theophlline and PE2. (p values reveal significance as determined by paired t-test).

FIG. 7 shows the change in $I_{SC}$ produced by pre-treatment of tissue with either PBS or bromelain. The data show that bromelain is effective in reducing the $I_{SC}$ and therefore secretion caused by theophylline and prostaglandins.

EXAMPLE 6

Effect of Bromelain on Secretion caused by a Calcium Dependent Pathway

Experiments were conducted in a similar manner as for those described in Example 4. Bromelain diluted in PBS (final concentration 15 ug/ml) were added to both sides of the ileal tissue. Control tissues were treated with PBS alone. Chambers were allowed to incubate for 30 minutes and rinsed as described above. A calcium ionophore (A23187) (final concentration $5\times10^{-7}$M) was added to the serosal side of the tissue. Ca ionophore causes the release of calcium from stores in the endoplasmic reticulum. Increased levels of $Ca^{2+}$ in the cell stimulates secretion by action on a $Ca^{2+}$-dependent pathway.

Figure 8:
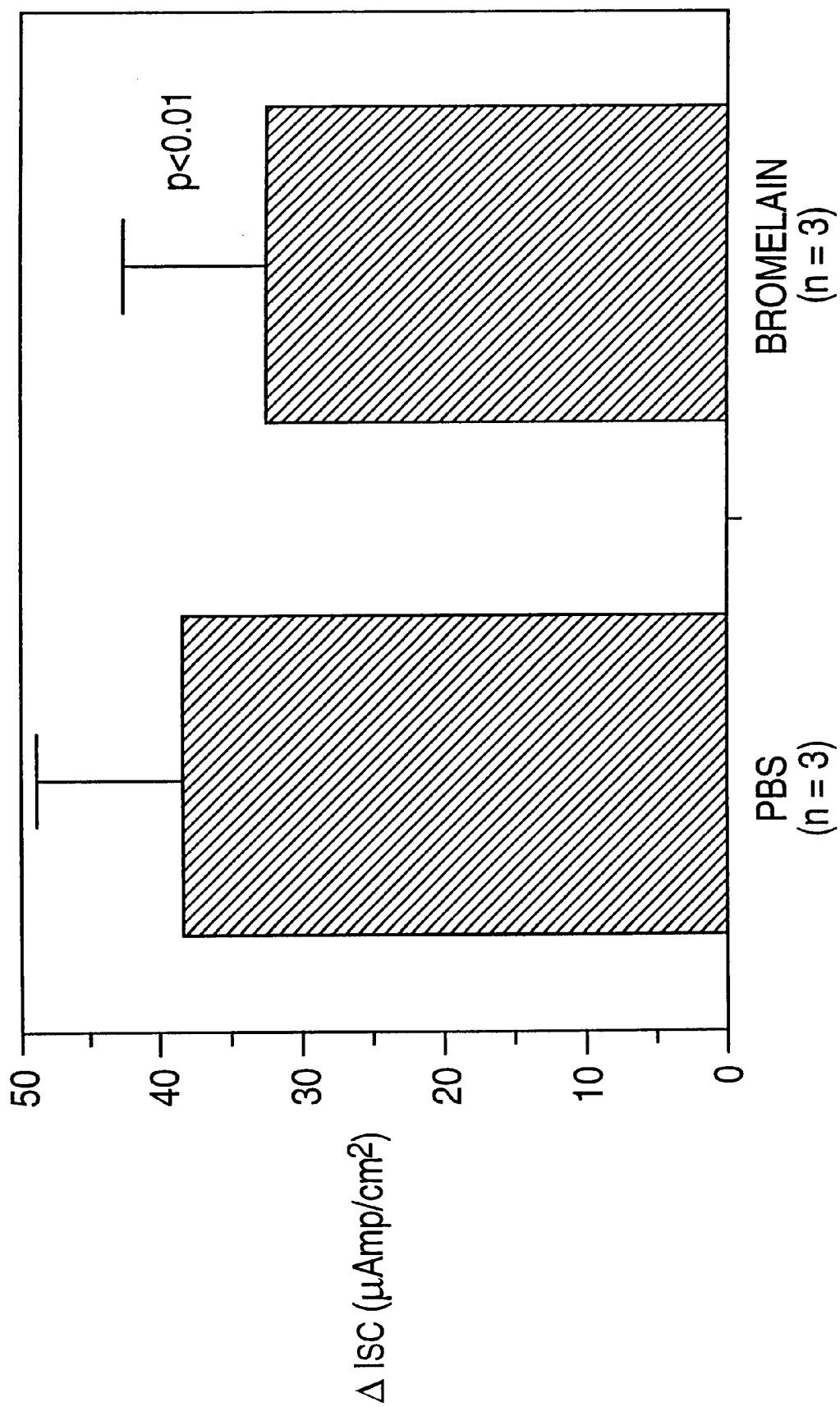
FIG. 8 shows the effect of pre-treatment of ileal tissue with PBS or bromelain on $I_{SC}$ changes caused by the calcium-ionophore A23187. (p values reveal significance as determined by paired t-test).

FIG. 8 shows the change in $I_{SC}$ produced by pre-treatment of tissue with either PBS or bromelain. The data show that bromelain is effective in reducing the $I_{SC}$ and therefore secretion caused by a Ca-dependent pathway.

EXAMPLE 7

Effect of Crude Bromelain on Normally Function of the Intestine

7a Increase in absorption of fluid

Experiments were conducted in a similar manner as for those described in Example 4. Bromelain diluted in PBS (final concentration 15 ug/ml) were added to both sides of the ileal tissue. Control tissues were treated with PBS alone. Chambers were allowed to incubate for 30 minutes and rinsed as described above. Tissue was continually bathed in the Ringer's solution for 90 minutes. The change in $I_{SC}$ during the 90 minutes was monitored to observe the effects of endogenous mediators of secretion (for example hormones, neurotransmitters and nutrients) and whether the tissue was absorbing or secreting.

Figure 9A:
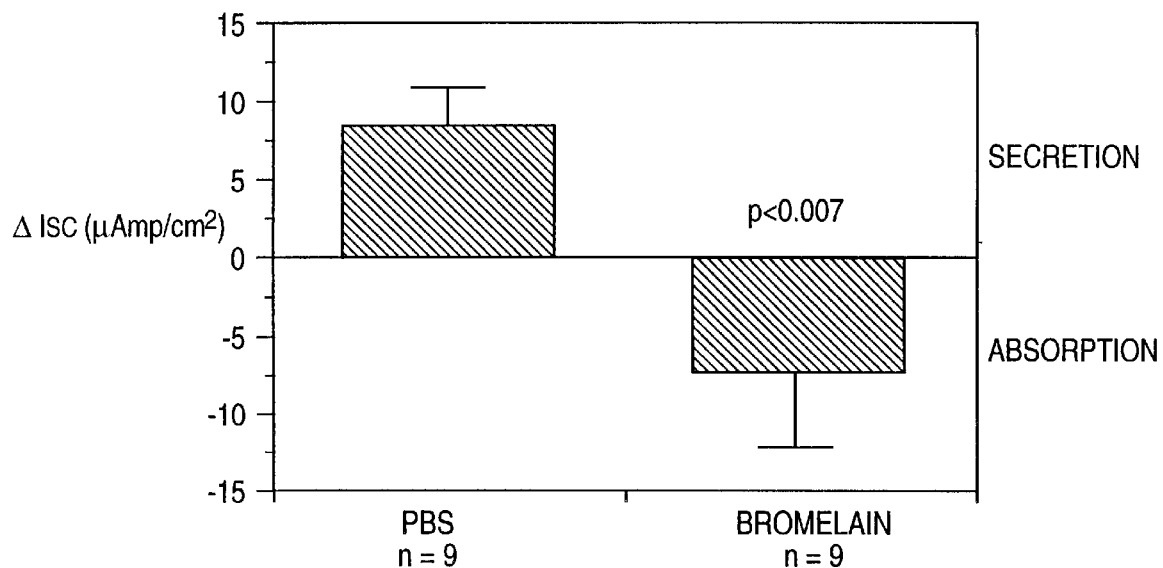
FIG. 9 shows the effect of pre-treatment of ileal tissue with PBS or bromelain on $I_{SC}$ changes caused by endogenous mediators of secretion and the ability of bromelain to stimulate absorption. (p values reveal significance as determined by paired t-test).
Figure 9B:
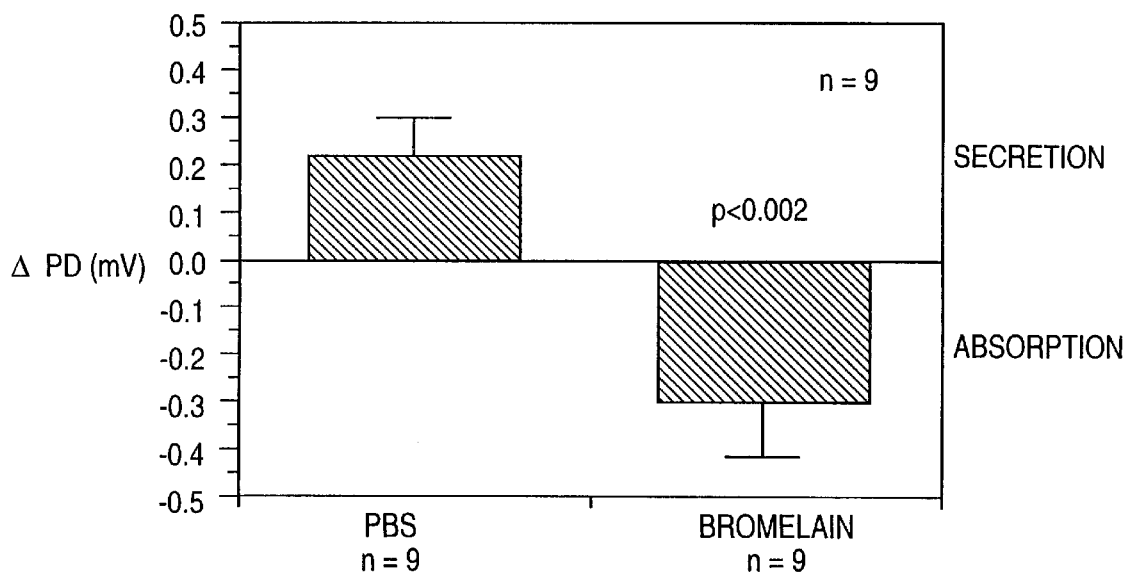

FIG. 9 shows the change in $I_{SC}$ produced by pre-treatment of tissue with either PBS or bromelain. The data show that bromelain treatment of tissue was effective in reducing the $I_{SC}$ induced by endogenous mediators of secretion and also was effective in stimulating absorption. The data demonstrate that bromelain is also effective against non-infectious diarrhoea. The fact that bromelain can inhibit secretion and enhance absorption is also a remarkable discovery in that it demonstrates that bromelain will be effective in both treating and preventing diarrhoea.

7b Increase in absorption of nutrients

These experiments were conducted to demonstrate the effect of bromelain on other physiologically important receptors required for nutrient uptake. These studies lead to the discovery that bromelain could also enhance the absorption of nutrients.

Influx Experiments. We tested glucose influx (initial rate of unidirectional flux of glucose from the incubation medium into the epithelium) in the presence and absence of bromelain (Guandalini, S. Fasano, A. Albibi, F. Marchesano, G. Nocerino, A. De Curtis, M. Rualtelli, F. F. Pettenazzo, A. & Rubino, A. (1988) *Gut*, 29, 366–371). Influx of the amino acids, glutamic acid, lysine, leucine and the di-peptide, glycine-phenylalanine, was also studied.

New Zealand White rabbits were killed by chloroform inhalation. A 25 cm segment of ileum, was excised, opened along the mesenteric border and rinsed free of intestinal contents with cold Ringer's solution. Two 10 cm segments of intestine were rapidly mounted in lucite influx chambers, where four adjacent portions of the mucosal side (surface area of 0.28 cm$^2$) were exposed to the preincubation solution for 30 minutes at 37° C. and gassed with 95% of $O_2$/5% of $CO_2$. The pre-incubation solutions contained bromelain at 1 mg/ml for studies observing glucose influx, and 15 $\mu$g/ml for amino acid and dipeptide influx. Control tissues were incubated with Ringer's alone. Studies commenced when the preincubation solution was replaced with solutions of same composition, but with the presence of $C^{14}$-labelled nutrient and $H^3$-Inulin as a marker of extracellular space. Incubation in this solution was for 45–50 seconds and was stopped by quickly removing the solutions containing label and adding cold 0.3M mannitol. Each piece of exposed tissue was then punched out, gently blotted on filter paper, homogenised in 10% trichloroacetic acid and centrifuged to sediment particulate matter. Aliquots of the supernatants were assayed for radioactivity with Hpb Beckman scintillation fluid, in a Beckman LS 7500 Beta-counter. Calculations were conducted as previously described (Rubino, A. Field, M. & Schwachmann, H. (1971), *J. Biol. Chem*, 246, 3542–3548).

Table 2 shows the effect of bromelain on nutrient influx. The data show that there is no interference with glucose and amino acid influx, indicating no adverse effects on other receptors important for nutrient uptake. The data also reveal that treatment of intestinal tissue increases the absorption of nutrients.

cellular material was suspended in 2 ml cold Tris-HCl (pH 7.4) and filtered through a 1 mm Buchner funnel to remove connective tissue and muscle fibres. The mucosal cell suspension was hypotonically disrupted by dilution (1:6) with cold distilled water and then homogenised in a SORVALL blender at full speed for 2 min. (The word SORVALL is a trade mark.) The microsomal fraction was then precipitated with concentrated $MgCl_2$ or solid $CaCl_2$ (final concentration 10 mM) and centrifuged at 2,900×g for 20 min. The pellet obtained was discarded and the supernatant fluid filtered through cheese cloth and re-centrifuged at 27,000×g for 30 min to pellet the crude brush border material. The supernatant fluid (S1) was retained and stored at −20° C. until required. The crude brush border material was suspended in 10 ml distilled water, to which 10 ml Tris-HCl (1.4M, pH 7.4) and NaCl (0.15M) were then added. The suspension

TABLE 2

| | Influence of bromelain on nutrient influx*. | | | | | | | |
|---|---|---|---|---|---|---|---|---|
| | Gly—Phe | Leucine | Lysine | Glut. Ac. | Glucose* | | | |
| | 1 mM | 1 mM | 5 mM | 1 mM | 1 mM | 5 mM | 10 mM | 20 mM |
| Bromelain** | 0.64 ± 0.07 (n = 6) | 1.11 ± 0.09 (n = 6) | 1.3 ± 0.14 (n = 6) | 0.33 ± 0.03 (n = 6) | 0.48 ± 0.36 (n = 3) | 0.87 ± 0.19 (n = 4) | 2.19 ± 1.01 (n = 4) | 1.7 ± 1.3 (n = 2) |
| Ringer | 0.51 ± 0.04 (n = 6) | 1.04 ± 0.09 (n = 6) | 0.90 ± 0.04 (n = 6) | 0.21 ± 0.03 (n = 6) | 0.61 ± 0.35 (n = 2) | 1.01 ± 0.36 (n = 4) | 1.48 ± 0.39 (n = 4) | 1.9 ± 0.61 (n = 4) |

*Data are means ± SE for n animals. Difference between means is not statistically significant.
**Concentration of bromelain used to treat cells for amino acid influx and glucose influx experiments was 10 μg/ml and 1 mg/ml, respectively.
Gly—Phe, glycine-phenylalanine; Glut. Ac., glutamic acid.

EXAMPLE 8

The Influence of Protease on Attachment of LT to Brush Border Vesicles in an Enzyme Immunoassay Similar procedures to that described by Laux et al (*Infection and Immunity* 52 18–25 (1986)) and Mouricout and Julien (1987) *Infection and Immunity* 55 1216–1223 were used. (These authors immobilised intestinal mucous preparations on wells and subsequently treated coated wells with enzyme; this was used to determine the effects of enzyme treatments on calf and mouse mucosal preparations in attempts to elucidate the nature of K99 and K88 receptors.)

In the current study, brush border vesicles (BBV) were used as the test material. BBV were first prepared and then immobilised on the solid phase as follows:

Briefly, crude mucus was obtained from human small intestine by means of a method derived from that of Laux et al, loc. cit. Brush border vesicles were subsequently prepared by the method of Chandler "Inherited Resistance to K88+ *Escherichia coli* in Pigs", PhD Thesis, La Trobe University, Bundoora, Victoria, Australia (1986)). This procedure was derived from the methods of Christiansen and Carlsen (*Biochim. Biophys. Acta*. 647 188–195 (1981)), Carlsen et al, *Biochim. Biophys. Acta*. 689 12–20 (1982)) and Schmitz et al, (*Biochim. Biophys. Acta*. 323 98–112 (1978)). The details are set out in the following paragraph.

Human intestinal jejunal material was thawed in cold Tris-HCl (12 mM, pH 7.4), the villous surface gently scraped with a microscope slide and scrapings suspended in WDB. The suspension was then centrifuged at 27,000×g for 15 min to remove particulate and cellular matter. Supernatant material, hereafter called crude mucus (CM), was retained and stored at −20° C. until required. The pelleted was homogenised with 5 strokes in a P/E homogeniser at 1,000 rpm and centrifuged at 27,000×g for 30 min. The pellet containing brush border vesicles (BBV) was suspended in PBS for testing by EIA and for antiserum (anti-BBV IgG production.

BBV were immobilised on the solid phase by means of a high pH-coating buffer. BBV 1:50 (v/v) were diluted in sodium bicarbonate buffer ($NaHCO_3/Na_2CO_3$; 0.1M, pH 9.6) and adsorbed to wells by incubation overnight at 4° C.

The effect of enzyme on LT-binding was then determined by inoculating BBV coated wells with papain diluted [0.1% to 0.00625% (w/v)] in PBS. The plates were incubated for 30 min at 37° C. and then washed and blocked and the assay completed in the usual manner. Pure LT (1 μg/ml) was used as the toxin preparation in the binding assay. Control experiments were conducted where BBV were incubated with enzyme plus inhibitor, or working dilution buffer (WDB) only (FIG. 15). WDB contains phosphate buffered saline (0.1M, pH 7.4, PBS) to which bovine serum albumin [0.25% (w/v), BSA], ethylenediamine tetra-acetic acid, disodium salt (1 mM, EDTA), polyoxyethylenesorbitan monolaurate [0.05% (v/v), Sigma, Tween 20] and $NaN_3$ [0.1% (w/v)] had been added.

The enzyme immunoassay used is illustrated in FIG. 11; details of it are as follows:

Routine assays consisted of BBV immobilised to the wells of microtitre plates. The immobilised BBV were used to bind *E. coli* LT toxin. The presence of bound toxin was then detected by adding in turn, rabbit anti-LT IgG, urease-conjugated sheep anti-rabbit IgG, and enzyme substrate solution.

Immobilisation of BBV on Solid Phase

Disposable polystyrene microtitre plates (Nunc Laboratories, Roskilde, Denmark) were used for all assays.

BBV [1:50 (v/v)] were diluted in sodium bicarbonate buffer (NaHCO$_3$/Na$_2$CO$_3$; 0.1M, pH 9.6) and adsorbed to wells by incubation overnight at 4° C. Typically, 100 µl was added to each well. Alternatively, plates could be coated by incubation for 2 h at 37° C. Coated plates could be stored at 4° C. for 1–2 weeks until required.

Active binding sites remaining on wells after coating were routinely blocked by incubation (30 min at 37° C.) with bovine serum albumin [1% (w/v), Sigma, BSA] dissolved in PBS.

Diluents and Washing Procedures

The buffers used in all EIA assays performed in microtitre plates were based on PBS (0.1M, pH 7.2). WDB was generally used as the diluent for suspending samples and reagents. WDB containing ovalbumin (from chicken egg) [1% (w/v), grade II, Sigma] was used as the diluent for enzyme conjugates. Optimum dilutions (for specific activity and economy) of coating agents, antigens, detection antibodies and conjugates were estimated by crossed (checkerboard) titrations.

All incubation steps, excluding the coating procedures, were performed at 37° C. for 30 min. Between each of the steps, supernatant liquid was removed from the wells which were then washed three times with washing buffer consisting of PBS to which Tween 20 [0.05% (v/v)] had been added. Prior to the incubation with substrate, wells were washed with distilled water to remove any effect of residual buffer on substrate (pH sensitive) solutions.

Use of Urease Conjugates and Substrate

Urease-conjugated sheep-anti-rabbit IgG (whole molecule) was purchased from Allelix and Sigma.

Urea substrate [0.008% (w/v) bromocresol purple pH indicator; 0.1% (w/v) urea; 0.00074% (w/v) disodium salt EDTA in dH$_2$O; pH 4.8] was used to detect the presence of bound conjugated (urease) enzyme, where a positive reaction was evident from a distinct colour change from yellow to purple (Chandler et al, 1982). This colour change is attributed to the action of urease enzyme on urea, resulting in production of ammonia and a consequent rise in pH. Colour development in wells was measured by means of a TITERTEK MULTISKAN TC plate reader (Eflab), as absorbance at 540 nm (A$_{540}$). (The expression TITERTEK MULTISKAN TC is a trade mark.)

The action of bound urease (and hence specific colour development) could be stopped by addition of aqueous of thiomersal [0.025% (w/v)] to test wells (10 µl/well).

Treatment of BBV with papain resulted in complete reduction of LT-binding activity. The effects of lower concentrations of enzyme and an endpoint of enzyme activity, however, were not determined. Incubation with enzyme and inhibitor or WDB only had negligible effect on EIA activity. It is possible that the disruptive effect of LT-attachment was not due to modification of BBV receptors, but due to effects of protease on the solid phase coating. In order to investigate this possibility, anti-BBV IgG was used to detect the presence of BBV after protease treatment (FIG. 13). Papain treatment of the BBV-coated solid phase resulted in a slight reduction in EIA activity. This was taken as an indication that the BBV solid phase was largely unaffected by protease treatment. The reduction in EIA activity observed after protease treatment of BBV was therefore largely due to the effect on LT receptors located on the BBV.

EXAMPLE 9

The Influence of Protease on Attachment of Intestinal Brush Border Vesicles (BBV) to Colonisation Factor Antigens (CFA) in the EIA The following experiments were designed to investigate the use of protease in preventing attachment of CFA-bacteria to human intestinal preparations using enzyme immunoassay (EIA) procedures. The immunoassay used is illustrated in FIG. 12.

To determine the effect of protease in preventing attachment to CFA-positive E. coli, BBV were pre-incubated with protease in a separate (uncoated) plate for 30 min at 37° C. prior to completion of the binding assay as follows.

CFA-positive E. coli bacteria were diluted (10$^9$ bacteria/ml) in sodium bicarbonate buffer and adsorbed to wells of a microtitre plate as described in Example 2. BBV were diluted in WDB [1:200 (v/v)] and inoculated into triplicate wells (100 µl) and incubated for 30 min at 37° C. The presence of intestinal material bound to the bacteria was detected by means of rabbit IgG raised against BBV (anti-BBV IgG). This detection antibody was used at a concentration of 1:100 and diluted, in WDB. Bound IgG was detected with urease-conjugated sheep-anti-rabbit IgG (whole molecule) diluted in WDB containing 1% (w/v) ovalbumin and the assay developed with urea substrate as described in Example 7. Plate washing and incubation procedures were as described in Example 7.

The effect of pre-incubation of BBV with increasing amounts of papain (EC 3.4.22.2) on CFA/II attachment and therefore EIA activity is illustrated in FIG. 14.

Treatment of BBV with papain resulted in an extensive reduction of BBV attachment to E. coli strains which were either CFA/I-positive H10407 or CFA/II-positive E4833 (FIG. 15). Interestingly, papain treatment also affected the non-CFA/I-mediated attachment of H10407P. Trypsin [Type IX, 13-17,000 BAEE units ml$^{-1}$; 0.05% (w/v); Sigma] pre-treatment of BBV also significantly (p<0.001) reduced the ability of BBV to attach to immobilised E. coli E4833. Trypsin treatment of BBV reduced EIA activity from 0.656±0.052 to 0.003±0.001.

The degree of inhibition of binding was dependent on the concentration of enzyme present. Typically, high concentrations of protease [>1% (w/v)] led to EIA activities of A$_{540}$>0.2±0.012, presumably because the enzyme had affected the coating on the plate. At concentrations of enzyme between 0.1% to 0.0063% (w/v), EIA activities were low (A540<0.1±0.004) indicating that the enzyme had inhibited the binding of CFA to BBV. At enzyme concentrations below 0.0005% (w/v), EIA activity began to increase, because of dilution of the enzyme.

Control experiments were conducted whereby a protease inhibitor [Papain Inhibitor (Antipain); Soybean Trypsin Inhibitor, Type II-S, Sigma] was included in wells to block activity of the enzyme. In these wells EIA activity was similar to that observed without enzyme present.

Effect of Protease Treatment on the Solid Phase

The potential disruptive effect of the protease on the bacteria-coated solid phase was determined by separately incubating the protease (and WDB as a control) in test wells prior to washing, blocking, incubation of BBV, and completion of the assay. H10407 CFA/1-positive coated wells were incubated with papain [diluted 1% (w/v) to 0.000625% (w/v) in PBS] or WDB only. (WDB is Working Dilution Buffer, containing phosphate buffered saline and BSA, as described in Example 7).

Such pre-treatment of wells with large amounts of protease [>0.1% (w/v)] resulted in reduced EIA activity of some samples by up to 50% (0.324±0.091) compared with the activity observed in wells that had been pre-incubated with WDB alone (0.615±0.021). Large amounts of protease incubated separately with BBV prior to addition to wells had also been shown to affect the EIA result (see above). Smaller amounts of protease had a negligible effect on EIA activity.

Although EIA activity of the assay was reduced following pre-treatment of test wells with large amounts of enzyme [>0.1% (w/v)], the activity in the most affected wells still greatly exceeded the activity exhibited in wells coated with CFA-negative bacteria. The usefulness of this system for determining the adhesive ability of BBV was thus not affected.

The effect of protease on the solid phase was far less than the effect of protease on the BBV. Incubation of BBV with protease prior to inoculation of the test wells, led to severe inhibition of the activity of the material. The affect of protease on attachment therefore, appeared to be due to modification of the bacterial receptors located on the BBV, and not due to an influence of protease on the bacteria-coated solid phase.

I claim:

1. A method of inhibiting increased intestinal fluid secretion induced by a non-bacterial secretagogue, comprising administering to a human or animal patient in need thereof a protease in an amount which is therapeutically effective in inhibiting the increased secretion.

2. The method of claim 1, wherein the protease is a cysteine protease.

3. The method of claim 1, wherein the protease is selected from the group consisting of bromelain, papain and trypsin.

4. The method of claim 1, wherein the protease is purified stem bromelain protease.

5. The method of claim 1, wherein the protease is further therapeutically effective in enhancing intestinal absorption of nutrients.

```
SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
          (A) LENGTH: 213 amino acids
          (B) TYPE: amino acid
          (C) STRANDEDNESS: single
          (D) TOPOLOGY: linear (xi) SEQUENCE DESCRIPTION: SEQ ID NO:1:

Ala Val Pro Gln Ser Ile Asp Trp Arg Asp Tyr Gly Ala Val Thr Ser
     1               5                   10                  15

Val Lys Asn Gln Asn Pro Cys Gly Ala Cys Trp Ala Phe Ala Ala Ile
                 20                  25                  30

Ala Thr Val Glu Ser Ile Tyr Lys Ile Lys Lys Gly Ile Leu Glu Pro
             35                  40                  45

Leu Ser Glu Gln Gln Val Leu Asp Cys Ala Lys Gly Tyr Gly Cys Lys
         50                  55                  60

Gly Gly Trp Glu Phe Arg Ala Phe Glu Phe Ile Ile Ser Asn Lys Gly
     65                  70                  75                  80

Val Ala Ser Gly Ala Ile Tyr Pro Tyr Lys Ala Ala Lys Gly Thr Cys
                     85                  90                  95

Lys Thr Asp Gly Val Pro Asn Ser Ala Tyr Ile Thr Gly Tyr Ala Arg
                 100                 105                 110

Val Pro Arg Asn Asn Glu Ser Ser Met Met Tyr Ala Val Ser Lys Gln
             115                 120                 125

Pro Ile Thr Val Ala Val Ala Asp Ala Asn Ala Asn Phe Gln Tyr Tyr
         130                 135                 140

Lys Ser Gly Val Phe Asn Gly Pro Cys Gly Thr Ser Leu Asn His Ala
     145                 150                 155                 160

Val Thr Ala Ile Gly Tyr Gly Gln Asp Ser Ile Ile Tyr Pro Lys Lys
                     165                 170                 175

Trp Gly Ala Lys Trp Gly Glu Ala Gly Tyr Ile Arg Met Ala Arg Asp
                 180                 185                 190

Val Ser Ser Ser Ser Gly Ile Cys Gly Ile Ala Ile Asp Pro Leu Tyr
             195                 200                 205

Pro Thr Leu Glu Glu
         210
```

6. A method of inhibiting increased intestinal fluid secretion induced by a non-bacterial secretagogue, comprising administering to a human or animal patient in need thereof purified stem bromelain protease, having the amino acid sequence of SEQ ID NO: 1, in an amount which is therapeutically effective in inhibiting the increased secretion.

7. A method of inhibiting increased intestinal fluid secretion induced by a non-bacterial secretagogue, comprising administering to a human or animal patient in need thereof purified stem bromelain protease, having an amino acid sequence substantially homologous to SEQ ID NO: 1 and retaining bromelain protease activity, in an amount which is therapeutically effective in inhibiting the increased secretion.

8. The method of any one of claims 1 to 7, wherein the protease is enteric protected.

\* \* \* \* \*